United States Patent

Misslitz et al.

[11] Patent Number: 5,330,965
[45] Date of Patent: Jul. 19, 1994

[54] CYCLOHEXENONE OXIME ETHERS AND THEIR USE AS HERBICIDES

[75] Inventors: Ulf Misslitz, Neustadt; Norbert Meyer, Ladenburg; Juergen Kast, Boehl-Iggelheim; Norbert Goetz, Worms; Albrecht Harreus, Ludwigshafen; Thomas Kuekenhoehner, Frankenthal; Bruno Wuerzer, Otterstadt; Helmut Walter, Obrigheim; Karl-Otto Westphalen, Speyer; Matthias Gerber, Mutterstadt, all of Fed. Rep. of Germany

[73] Assignee: BASF Aktiengesellschaft, Ludwigshafen, Fed. Rep. of Germany

[21] Appl. No.: 981,492

[22] Filed: Jan. 15, 1993

Related U.S. Application Data

[62] Division of Ser. No. 697,040, May 8, 1991, Pat. No. 5,228,896.

[30] Foreign Application Priority Data

May 9, 1990 [DE] Fed. Rep. of Germany ....... 4014987

[51] Int. Cl.$^5$ ............... A01N 43/42; A01N 43/10; A01N 43/08; C07D 333/22
[52] U.S. Cl. .................... 504/244; 504/289; 504/294; 546/286; 546/300; 546/309; 546/311; 546/312; 546/326; 546/334; 546/335; 549/61; 549/65; 549/69; 549/71; 549/77; 549/474; 549/479; 549/480; 549/484; 549/494; 549/496
[58] Field of Search .......... 504/289, 294, 244; 549/75, 77, 65, 60, 59, 68, 473, 480, 496, 61, 69, 71, 474, 479, 484, 494; 546/335, 286, 300, 309, 311, 312, 326, 334

[56] References Cited

U.S. PATENT DOCUMENTS

| | | | |
|---|---|---|---|
| 4,432,786 | 2/1984 | Loh | 71/90 |
| 4,440,566 | 4/1984 | Luo | 504/315 |
| 4,624,969 | 11/1986 | Keil et al. | 504/292 |
| 4,812,160 | 3/1989 | Jahn et al. | 504/292 |
| 4,880,456 | 11/1989 | Kolassa et al. | 504/271 |
| 5,022,914 | 6/1991 | Kast et al. | 504/289 |

FOREIGN PATENT DOCUMENTS 218233 4/1987 European Pat. Off. .

Primary Examiner—Richard L. Raymond
Attorney, Agent, or Firm—Keil & Weinkauf

[57] ABSTRACT

Cyclohexenone oxime ethers of the formula I

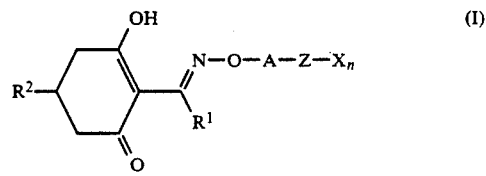

($R^1 = C_1$–$C_6$-alkyl;
A = substituted or unsubstituted alkylene or alkenylene;
Z = a 5-membered or 6-membered heteroaromatic structure;
X = substituted or unsubstituted amino, nitro, cyano, halogen, alkyl, $C_1$–$C_4$-alkoxy, $C_1$–$C_4$-alkylthio, $C_1$–$C_4$-haloalkyl, $C_1$–$C_4$-haloalkoxy, carboxyl, $C_1$–$C_4$-alkoxycarbonyl, substituted or unsubstituted benzyloxycarbonyl and phenyl;
n = 0 to 3, or 1 to 4 where Z is halogen-substituted pyridyl; and
$R^2$ = alkoxyalkyl or alkylthioalkyl; substituted or unsubstituted cycloalkyl or cycloalkenyl; a substituted or unsubstituted 5-membered saturated heterocyclic structure which contains one or two hetero atoms; a substituted or unsubstituted 6-membered or 7-membered saturated or mono- or diunsaturated heterocyclic structure containing one or two hereto atoms; a substituted or unsubstituted 5-membered heteroaromatic structure containing one to three hereto atoms; substituted or unsubstituted phenyl or pyridyl)

and their agriculturally useful salts and esters of $C_1$–$C_{10}$-carboxylic acids and inorganic acids.

The compounds are suitable as herbicides.

3 Claims, No Drawings

CYCLOHEXENONE OXIME ETHERS AND THEIR USE AS HERBICIDES

This is a division application Ser. No. 697,040, filed May, 8, 1991, now U.S. Pat. No. 5,228,896.

The present invention relates to novel herbicidal cyclohexenone oxime ethers of the formula I

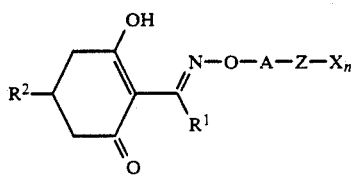

where
$R^1$ is $C_1$-$C_6$-alkyl;
A is $C_2$-$C_6$-alkylene or $C_3$-$C_6$-alkenylene, where these groups may carry from one to three $C_1$-$C_3$-alkyl groups or halogen atoms;
Z is a 5-membered heteroaromatic structure having from one to three hetero atoms selected from the group consisting of three nitrogen atoms and one oxygen or sulfur atom or a 6-membered heteroaromatic structure having from one to four nitrogen atoms;
X is an amino group —$NR^aR^b$, where
$R^a$ is hydrogen, $C_1$-$C_4$-alkyl, $C_3$-$C_6$-alkenyl or $C_3$-$C_6$-alkynyl and
$R^b$ is hydrogen, $C_1$-$C_4$-alkyl, $C_3$-$C_6$-alkenyl, $C_3$-$C_6$-alkynyl, $C_1$-$C_6$-acyl or benzoyl, where the aromatic ring may additionally carry from one to three of the following substituents: nitro, cyano, halogen, $C_1$-$C_4$-alkyl, $C_1$-$C_4$-alkoxy, $C_1$-$C_4$-alkylthio and $C_1$-$C_4$-haloalkyl, or X is nitro, cyano, halogen, $C_1$-$C_4$-alkyl, $C_1$-$C_4$-alkoxy, $C_1$-$C_4$-alkylthio, $C_1$-$C_4$-haloalkyl, $C_1$-$C_4$--haloalkoxy, carboxyl, $C_1$-$C_4$-alkoxycarbonyl, benzyloxycarbonyl or phenyl, where the aromatic radicals may additionally carry from one to three of the following substituents: nitro, cyano, halogen, $C_1$-$C_4$-alkyl, $C_1$-$C_4$-alkoxy, $C_1$-$C_4$-alkylthio, $C_1$-$C_4$-haloalkyl, $C_1$-$C_4$-haloalkoxy, carboxyl, $C_1$-$C_4$-alkoxycarbonyl or benzyloxycarbonyl,
n is from 0 to 3, or from 1 to 4 where Z is halogensubstituted pyridyl, and
$R^2$ is $C_1$-$C_4$-alkoxy-$C_1$-$C_6$-alkyl or $C_1$-$C_4$-alkylthio-$C_1$-$C_6$-alkyl;
$C_3$-$C_7$-cycloalkyl or $C_5$-$C_7$-cycloalkenyl, where these groups may additionally carry from one to three radicals selected from the group consisting of $C_1$-$C_4$-alkyl, $C_1$-$C_4$-alkoxy, $C_1$-$C_4$-alkylthio, $C_1$-$C_4$-haloalkyl hydroxyl and halogen;
a 5-membered saturated heterocyclic structure which contains one or two hetero atoms selected from the group consisting of oxygen and sulfur, where the heterocyclic structure may additionally carry from one to three radicals selected from the group consisting of $C_1$-$C_4$alkyl, $C_1$-$C_4$-alkoxy, $C_1$-$C_4$-alkylthio and $C_1$-$C_4$-haloalky;
a 6-membered or 7-membered saturated or mono- or diunsaturated heterocyclic structure containing one or two hetero atoms selected from the group consisting of oxygen and sulfur, where this ring may additionally carry from one to three radicals selected from the group consisting of hydroxyl, halogen, $C_1$-$C_4$-alkyl, $C_1$-$C_4$-alkoxy, $C_1$-$C_4$-alkylthio and $C_1$-$C_4$haloalkyl;
a 5-membered heteroaromatic structure containing one to three hetero atoms selected from the group consisting of two nitrogen atoms and one oxygen or sulfur atom, where this ring may additionally carry from one to three radicals selected from the group consisting of halogen, cyano, $C_1$-$C_4$-alkyl, $C_1$-$C_4$-alkoxy, $C_1$-$C_4$-alkylthio, $C_1$-$C_4$-haloalkyl; $C_2$-$C_6$-alkenyl, $C_2$-$C_6$-alkenyloxy, $C_2$-$C_6$-haloalkenyl and $C_1$-$C_4$-alkoxy-$C_1$-$C_4$-alkyl, or phenyl or pyridyl, where these groups may additionally carry from one to three radicals selected from the group consisting of halogen, nitro, cyano, $C_1$-$C_4$-alkyl, $C_1$-$C_4$-alkoxy, $C_1$-$C_4$-alkylthio, $C_1$-$C_4$-haloalkyl, $C_1$-$C_4$-alkenyloxy, $C_3$-$C_6$-alkynyloxy and —$NR^aR^b$, where $R^a$ and $R^b$ have the abovementioned meanings,
and their agriculturally useful salts and esters of $C_1$-$C_{10}$-carboxylic acids and inorganic acids.

The present invention furthermore relates to a process and intermediates for their preparation and to their use as crop protection agents.

The novel cyclohexenones I are evidently acidic, i.e. they can form simple reaction products, such as salts of alkali metal or alkaline earth metal compounds or enol esters.

The compounds of the formula I may occur in a plurality of tautomeric forms, all of which are embraced by the claims.

The literature describes cyclohexenones of the general formula I'

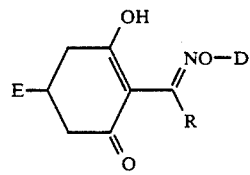

where, inter alia,
D is benzyl and E is 2-ethylthiopropyl (US-A 4 440 566);
D is benzyl or but-2-enyl and E is a substituted 5-membered heteroaryl radical (EP-A 238 021 and EP-A 125 094);
D is benzyl or but-2-enyl and E is substituted phenyl (EP-A 80 301) or
D is but-2-enyl and E is a 5-membered to 7-membered heterocyclic ring having up to two O or S atoms and up to two double bonds (EP-A 218 233),
as herbicides.

It is an object of the present invention to provide compounds which have high selectivity at a low application rate, i.e. control undesirable plants without damaging the crops.

We have found that this object is achieved by the novel cyclohexenone oxime ethers of the formula I, which have a good herbicidal action against undesirable grasses. The compounds are tolerated by broad-leaved crops and some are tolerated by gramineous crops, such as rice.

The cyclohexenones of the formula I can be prepared in a conventional manner from known derivatives of the formula II (EP-A 80 301, EP-A 125 094, EP-A 142 741, US-A 4 249 937, EP-A 137 174 and EP-A 177 913) and the corresponding hydroxylamines of the formula III (Houben-Weyl, 10/1, page 1181 et seq.) (EP-A 169 521).

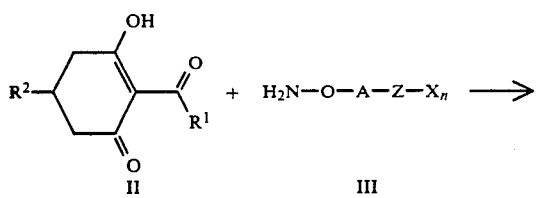

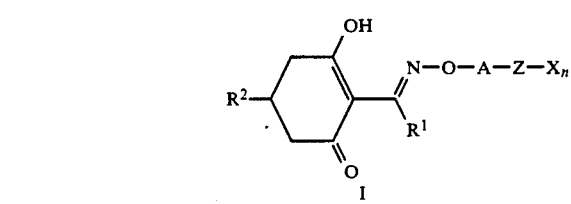

The reaction is advantageously carried out in the heterogeneous phase in a solvent at an adequate temperature below about 80° C. in the presence of a base, and the hydroxylamine III is used in the form of its ammonium salt.

Examples of suitable bases are carbonates, bicarbonates, acetates, alcoholates or oxides of alkali metals or of alkaline earth metals, in particular sodium hydroxide, potassium hydroxide, magnesium oxide and calcium oxide. Organic bases, such as pyridine or tertiary amines, can also be used. The base is added, for example in an amount of from 0.5 to 2 mol equivalents, based on the ammonium compound.

Examples of suitable solvents are dimethyl sulfoxide, alcohols, such as methanol, ethanol and isopropanol, aromatic hydrocarbons, such as benzene and toluene, chlorohydrocarbons, such as chloroform and dichloroethane, aliphatic hydrocarbons, such as hexane and cyclohexane, esters, such as ethyl acetate, and ethers, such as diethyl ether, dioxane and tetrahydrofuran. The reaction is preferably carried out in methanol, using sodium bicarbonate as the base.

The reaction is complete after a few hours. The desired compound can be isolated, for example, by evaporating down the mixture, partitioning the residue in methylene chloride/water and distilling off the solvent under reduced pressure.

For this reaction it is however also possible to use the free hydroxylamine base directly, for example in the form of an aqueous solution; a single-phase or two-phase reaction mixture is obtained, depending on the solvent used for compound II.

Suitable solvents for this variant are, for example, alcohols, such as methanol, ethanol, isopropanol and cyclohexanol, aliphatic and aromatic hydrocarbons and chlorohydrocarbons, such as hexane, cyclohexane, methylene chloride, toluene and dichloroethane, esters, such as ethyl acetate, nitriles, such as acetonitrile, and cyclic ethers, such as dioxane and tetrahydrofuran.

Alkali metal salts of the compounds I can be obtained by treating the 3-hydroxy compounds with sodium hydroxide, potassium hydroxide, a sodium alcoholate or potassium alcoholate in aqueous solution or in an organic solvent, such as methanol, ethanol, acetone or toluene.

Other metal salts, such as manganese, copper, zinc, iron, calcium, magnesium and barium salts, can be prepared from the sodium salts in a conventional manner, as can ammonium and phosphonium salts using ammonia or phosphonium, sulfonium or sulfoxonium hydroxides.

The compounds of type II can be prepared, for example, from the corresponding cyclohexane-1,3-diones of the formula IV

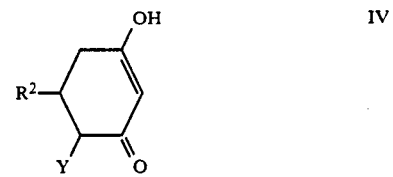

where Y is hydrogen or methoxycarbonyl, by known methods (Tetrahedron Lett. (1975), 2491).

It is also possible to prepare the compounds of the formula II via the enol ester intermediates, which are obtained in the reaction of compounds of the formula IV with acyl chlorides in the presence of a base and are then subjected to a rearrangement reaction with certain imidazole or pyridine derivatives (Japanese Preliminary Published Application 79/063 052).

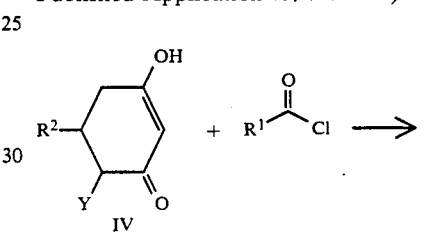

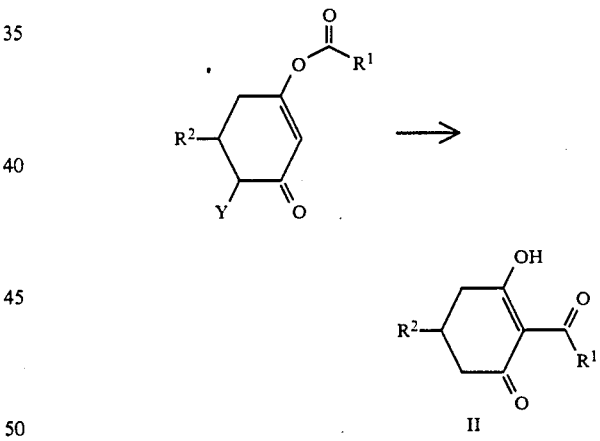

IV The compounds of the formula IV are obtained via a number of known process steps, starting from known precursors.

The hydroxylamines III in which A is an unsubstituted but-3-enylene bridge are synthesized in accordance with the reaction scheme below:

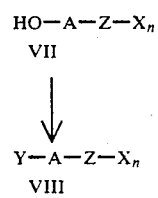

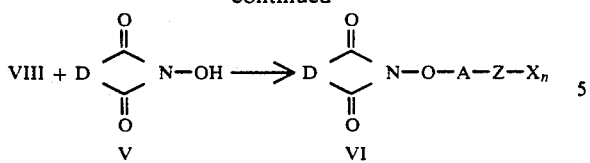

Y=Leaving group, e.g. halogen, such as chlorine, bromine and iodine, or CH$_3$SO$_2$—O—.

The alkylating agents VIII can be prepared by conventional methods [cf. Umlagerung von Cyclopropylhetarylcarbinolen: J. Heterocycl. Chem. 14 (1976), 525, JP 55 051 004, JP 55 047 601; Houben-Weyl: Methoden der Organischen Chemie, Volume 4/3, page 424 et seq.; Kupplung metallierter Heterocyclen mir 1,ω-Dibromalkanen: DE-A 2821409, and Chem. Ber. 114 (1981) 3667 and 3674].

If desired, the alkylating agents VIII can be obtained in a conventional manner from the carbinols VII [Kupplung von Hetaryliodiden, -bromiden mir 1,ω-Alkenolen in Gegenwart von Palladiumkatalysatoren: Tetrahedron 35 (1979), 329; Chem. Lett. (1977), 423; Houben-Weyl: Methoden der Organischen Chemie, Volume 13/93, page 964 et seq.] [cf. Houben-Weyl: Methoden der Organischen Chemie, Volume 5/3, page 862 et seq. and page 899 et seq. and ibid., Volume 5/4, page 361 et seq.]

The alkylating agent is preferably coupled with a cyclic hydroximide V and the resulting protected hydroxylamine derivative VI is cleaved to give the free hydroxylamine III, for example with 2-aminoethanol.

In the cyclic hydroximides V, D is, for example, C$_2$-C$_3$-alkylene, C$_2$-alkenylene or a 5-membered or 6-membered ring which contains up to 3 double bonds and may contain 1 nitrogen atom, for example phenylene, pyridinylene, cyclopentylene or cyclohexylene or cyclohexenylene. Examples of suitable substances are the following:

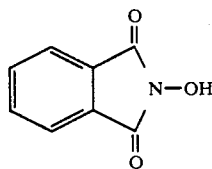

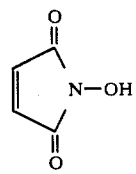

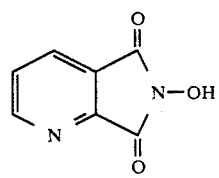

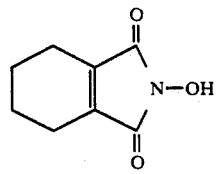

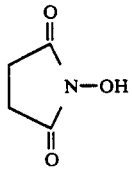

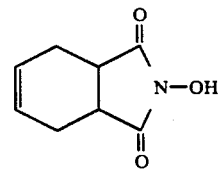

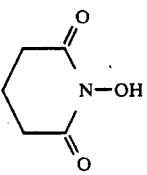

The reaction of the compounds VIII with the hydroximides V is advantageously carried out in the presence of a base. All bases capable of deprotonating the hydroximides V without attacking the imide system are in principle suitable. These are, in particular, the non-nucleophilic bases. Examples are mineral bases, such as alkali metal and alkaline earth metal carbonates, alkali metal and alkaline earth metal bicarbonates and organic bases, such as aliphatic, cycloaliphatic and aromatic tertiary amines. Mixtures of these bases can also be used.

Examples of individual compounds are the following bases: sodium carbonate, potassium carbonate, magnesium carbonate, calcium carbonate and barium carbonate, the bicarbonates of these metals, trimethylamine, triethylamine, tributylamine, ethyl diisopropylamine, N,N-dimethylaniline, 4-N,N-dimethylaminopyridine, diazabicyclooctane, diazabicycloundecane, N-methylpiperidine, 1,4-dimethylpiperazine, pyridine, quinoline, bipyridine and phenanthroline. The economical bases sodium-carbonate and potassium carbonate are preferred.

The base is generally added in from equivalent amounts to an excess of 5 equivalents, based on the hydroximide. A greater excess is possible but has no additional advantages. The use of a small amount of base is also possible. However, the base is preferably used in an amount of from 1 to 3, in particular from 1 to 2, equivalents, based on the hydroximide V.

It is also possible to use nucleophilic bases, for example alkali metal and alkaline earth metal hydroxides, in particular sodium hydroxide and potassium hydroxide. In this case, it is advantageous to use the base in equivalent amounts, based on the hydroximide V, in order to prevent a nucleophilic attack by the hydroxyl ions on the carbonyl function of the imide group.

The starting compounds VIII are advantageously reacted with the hydroximides V in a solvent which is inert under the reaction conditions. Examples of advantageous solvents are polar aprotic solvents, such as dimethylformamide, N-methylpyrrolidone, dimethyl sulfoxide, sulfolane and cyclic ureas. The amount of solvent is in general not critical.

The reaction of the starting compounds VIII with the hydroximides V can also be carried out using phase transfer catalysis. In this case, solvents, preferably chlorohydrocarbons, which form two phases with water are used. Suitable phase transfer catalysts are the quaternary ammonium and phosphonium salts, polyethylene glycols, polyethylene glycol ethers and crown ethers usually used for such purposes and as described in, for example, Dehmlow et al., Phase Transfer Catalysis, pages 37–45 and pages 86–93, Verlag Chemie, Weinheim 1980. The phase transfer catalysts are advantageously used in amounts of from 1 to 10, preferably from 3 to 5, % by volume, based on the volume of the reaction mixture.

The reaction of the starting compounds VIII with the hydroximides V is carried out in general at from 0° to 140° C., preferably from 20° to 100° C., in particular from 40 to 80° C. In an advantageous procedure, the hydroximide V is initially taken together with the base in the solvent, and the starting material VIII is metered into the solution. It may prove advantageous if the hydroximide is added at a lower temperature, for example at from 0° to 50° C., and the reaction mixture is not heated to the actual reaction temperature until this addition is complete.

After the end of the reaction, water is advantageously added to the cooled reaction mixture, the resulting hydroxylamine derivatives VI separating out as crystalline solids or as oils. The hydroxylamine derivatives obtained in this manner can, if desired, be further purified by recrystallization or by extraction.

The hydroxylamine derivatives VI can be temporarily stored or can be converted immediately into the hydroxylamine derivatives III having a free amino group.

This conversion can be carried out by conventional processes, as described, for example, in DE-A 36 15 973 and the publications cited therein. The process according to DE-A 36 15 973 is preferably used, in which the hydroxylamine derivatives III are liberated by means of ethanolamine. Liberation of the hydroxylamine derivatives III with the aid of other bases, such as aqueous mineral bases, with amines, hydrazines or hydroxylamines or by means of aqueous acids, is also possible.

The hydroxylamine derivatives III can be isolated from the reaction mixtures obtained in this process by means of conventional working up methods, for example by extraction or by crystallization. To increase the tendency of these hydroxylamine derivatives to crystallize, it may often be necessary to convert them into their salts with mineral acids or organic acids. Dilute solutions of these acids are generally reacted with the hydroxylamine derivatives for this purpose, advantageously in equivalent amounts. The resulting hydroxylammonium salts can, like the hydroxylamine derivatives having a free amino group, be further processed directly to the herbicides of the formula I or, if desired, stored.

With regard to the biological activity, preferred cyclohexenones of the formula I are those in which the substituents have the following meanings: $R^1$ is alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, in particular ethyl or propyl;

A is alkylene or alkenylene, such as ethylene, propylene, prop-2-enylene, butylene, but-2-enylene, but-3-enylene, pentylene, pent-4-enylene, hexylene or hex-5-enylene, where the stated groups may be monosubstituted to trisubstituted by, in particular, methyl or ethyl and/or fluorine or chlorine; in the unsaturated chains, both the cis and the trans form may occur; but-2-enylene and but-3-enylene are particularly preferred;

Z is 5-membered hetaryl, such as furanyl, pyrrolyl, thienyl, imidazolyl, pyrazolyl, isoxazolyl, oxazolyl, isothiazolyl, thiazolyl, oxadiazolyl, thiadiazolyl or triazolyl, in particular furanyl or thienyl, or 6-membered hetaryl, such as pyridyl, pyridazyl, pyrimidyl, pyrazyl, triazyl or tetrazyl, in particular pyridyl or pyrimidyl;

X is nitro, cyano, halogen, such as fluorine, chlorine, bromine or iodine, in particular fluorine or chlorine, alkyl, such as methyl, ethyl, propyl, 1-methylethyl, butyl, 1-methylpropyl, 2-methylpropyl or 1,1-dimethylethyl, in particular methyl or 1,1-dimethylethyl, alkoxy, such as methoxy, ethoxy, propoxy, 1-methylethoxy, butoxy, 1-methylpropoxy, 2-methylpropoxy or 1,1-dimethylethoxy, in particular methoxy, ethoxy, 1-methylethoxy or 1,1-dimethylethoxy, alkylthio, such as methylthio, ethylthio, propylthio, 1-methylethylthio, butylthio, 1-methylpropylthio, 2-methylpropylthio or 1,1-dimethylethylthio, in particular methylthio or ethylthio, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl, haloalkoxy, such as difluoromethyl, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy, carboxyl, alkoxycarbonyl, such as methoxycarbonyl, ethoxycarbonyl, propoxycarbonyl, 1-methylethoxycarbonyl, butoxycarbonyl or 1,1-dimethylethoxycarbonyl, in particular methoxycarbonyl, ethoxycarbonyl or 1,1-dimethylethoxycarbonyl, especially methoxycarbonyl, benzyloxycarbonyl or phenyl, where the aromatic radicals in turn may carry from one to three of the following radicals: nitro, cyano, carboxyl, benzyloxycarbonyl, halogen as stated in general and in particular for X, alkyl as stated for $R^1$, in particular methyl, ethyl or 1-methylethyl, alkoxy as stated above, in particular methoxy or ethoxy, alkylthio as stated above, in particular methylthio, haloalkyl as stated above, in particular trifluoromethyl, haloalkoxy as stated above, in particular difluoromethoxy or trifluoromethoxy, and/or alkoxycarbonyl as stated above, in particular methoxycarbonyl or ethoxycarbonyl, an amino group —$NR^aR^b$, where $R^a$ is hydrogen, alkyl, such as methyl, ethyl, propyl, 1-methylethyl, butyl, 1-methylpropyl, 2-methylpropyl or 1,1-dimethylethyl, in particular methyl or ethyl, alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,3-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl 1,1-dimethyl-2-butenyl, 1,1-dimethyl-3-butenyl, 1,2-dimethyl-2-butenyl, 1,2-di-methyl-3-butenyl, 1,3-dimethyl-2-butenyl, 1,3-dimethyl-3-butenyl, 2,2-dimethyl-3-butenyl, 2,3-dimethyl-2-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl or 2-butenyl, and $R^b$ is hydrogen, alkyl as stated above in general and in particular, alkenyl as stated above in general and in particular, alkynyl, such as 2-propynyl, 2-butynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, in particular 2-propynyl or 2-butynyl; acyl, such as acetyl, propionyl, butyryl, 2-methylpropionyl, pentanoyl, 2-methylbutyryl, 3-methylbutyryl, 2,2-dimethylpropionyl, hexanoyl, 2-methylpentanoyl, 3-methylpentanoyl, 4-methylpentanoyl, 2,2-dimethylbutyryl, 2,3-dimethylbutyryl, 3,3-dimethylbutyryl or 2-ethylbutyryl, in particular acetyl or propionyl, or benzoyl, where the aromatic radical may carry from one to three of the following radicals: nitro, cyano, carboxyl, benzyloxycarbonyl, halogen as stated in general and in particular for X, alkyl as stated for $R^1$, in particular methyl or ethyl or 1-methylethyl, alkoxy as stated above, in particular methoxy or ethoxy, alkylthio as stated above, in particular methylthio, haloalkyl as stated above, in particular trifluoromethyl, haloalkoxy as stated above, in particular difluoromethoxy or trifluoromethoxy, and/or alkoxycarbonyl as stated above, in particular methoxycarbonyl or ethoxycarbonyl;

n is 0, 1, 2 or 3, in particular 0, 1 or 2, and when Z is halogen-substituted pyridyl is from 1 to 4; n is preferably 0, 1 or 2; where there is a plurality of radicals X, the substituents may be identical or different;

R2 is alkyl as stated under X, or pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, which are substituted, preferably in the 1-, 2- or 3-position, by one of the alkoxy or alkylthio groups stated under X, in particular-2-ethylthiopropyl, 5-membered heterocycloalkyl, such as tetrahydrofuranyl, tetrahydrothienyl, dioxolanyl, dithiolanyl or oxathiolanyl, in particular tetrahydrofuranyl, tetrahydrothienyl or dioxolanyl, where these rings may carry from one to three of the $C_1$–$C_4$-alkyl, $C_1$–$C_4$-alkoxy, $C_1$–$C_4$-alkylthio and/or $C_1$–$C_4$-haloalkyl groups stated above under X, 5-membered hetaryl, such as pyrrolyl, pyrazolyl, imidazolyl, isoxazolyl, oxazolyl, isothiazolyl, thiazolyl, furanyl or thienyl, in particular isoxazolyl or furanyl, a 6-membered or 7-membered heterocyclic structure, such as tetrahydropyran-3-yl, dihydropyran-3-yl, tetrahydropyran-4-yl, dihydropyran-4-yl, tetrahydrothiopyran-3-yl, dihydrothiopyran-3-yl, tetrahydrothiopyran-4-yl, dihydrothiopyran-4-yl or dioxepan-5-yl, in particular tetrahydropyran-3-yl, tetrahydropyran-4-yl or tetrahydrothiopyran-3-yl, phenyl or pyridyl, where the cyclic radicals may carry from one to three of the alkyl, alkoxy, alkylthio and/or haloalkyl groups stated under X.

The 5-membered heteroaromatic structures R2 may carry the following radicals as substituents: halogen as stated under X, in particular fluorine or chlorine, alkoxyalkyl, such as methoxymethyl, 2-methoxyethyl, 2-methoxypropyl, 3-methoxypropyl, 2-methyl-1-methylethyl, ethoxymethyl, 2-ethoxyethyl, 2-ethoxypropyl, 3-ethoxypropyl, 2-ethoxy-1-methylethyl or 1-ethoxy-1-methylethyl, in particular methoxyethyl or ethoxyethyl, alkenyl, such as ethenyl, 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl or 1-ethyl-2-methyl-2-propenyl, in particular 1-methylethenyl, or corresponding alkenyloxy and/or haloalkenyl radicals.

The 6-membered and 7-membered heterocyclic structures may also carry hydroxyl in addition to the abovementioned substituents.

In the case of the phenyl and pyridyl radicals, suitable substituents in addition to the abovementioned groups are the following radicals: alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl- 3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl - 3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 1,1-dimethyl-2-butenyloxy, 4-methyl-4-pentenyloxy, 1,1-dimethyl-2-butenyloxy, 1,1,dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy or 1-ethyl-2-methyl-2-propenyloxy, in particular 2-propenyloxy or 2-butenyloxy; alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl - 3-pentynyloxy, 1-methyl-4-pentynyloxy, 2-methyl- 3-pentynyloxy, 2-methyl-4-pentynyloxy, 3-methyl - 4-pentynyloxy, 4-methyl-2-pentynyloxy, 1,1-dimethyl-2-butynyloxy, 1,1-dimethyl--3-butynyloxy, 1,2-dimethyl- 3-butynyloxy, 2,2-dimethyl-3-butynyloxy, 1-ethyl - 2-butynyloxy, 1-ethyl - 3-butynyloxy, 2-ethyl-3-butynyloxy or 1-ethyl-1-methyl-2-propynyloxy, in particular 2-propynyloxy or 2-butynyloxy, or $-NR^aR^b$ as stated in general and in particular for X.

Particularly preferred cyclohexenone oxime ethers of the formula I are summarized in the Tables below.

TABLE A

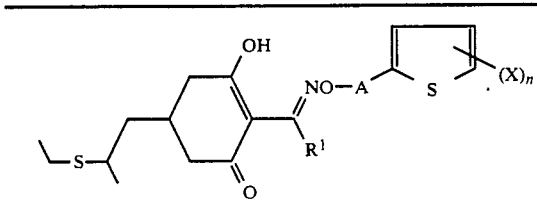

| R¹ | A | X | n |
|---|---|---|---|
| CH₂CH₃ | (CH₂)₂ | — | 0 |
| (CH₂)₂CH₃ | (CH₂)₂ | — | 0 |
| CH₂CH₃ | (CH₂)₂ | 5-Cl | 1 |
| (CH₂)₂CH₃ | (CH₂)₂ | 5-Cl | 1 |
| CH₂CH₃ | (CH₂)₂ | 5-CH₃ | 1 |
| (CH₂)₂CH₃ | (CH₂)₂ | 5-CH₃ | 1 |

TABLE A-continued

| R¹ | A | X | n |
|---|---|---|---|
| CH₂CH₃ | (CH₂)₂ | 5-C₂H₅ | 1 |
| (CH₂)₂CH₃ | (CH₂)₂ | 5-C₂H₅ | 1 |
| CH₂CH₃ | (CH₂)₃ | — | 0 |
| (CH₂)₂CH₃ | (CH₂)₃ | — | 0 |
| CH₂CH₃ | (CH₂)₃ | 5-Cl | 1 |
| (CH₂)₂CH₃ | (CH₂)₃ | 5-Cl | 1 |
| CH₂CH₃ | (CH₂)₃ | 5-CH₃ | 1 |
| (CH₂)₂CH₃ | (CH₂)₃ | 5-CH₃ | 1 |
| CH₂CH₃ | (CH₂)₃ | 5-C₂H₅ | 1 |
| (CH₂)₂CH₃ | (CH₂)₃ | 5-C₂H₅ | 1 |
| CH₂CH₃ | (CH₂)₄ | — | 0 |
| (CH₂)₂CH₃ | (CH₂)₄ | — | 0 |
| CH₂CH₃ | (CH₂)₄ | 5-Cl | 1 |
| (CH₂)₂CH₃ | (CH₂)₄ | 5-Cl | 1 |
| CH₂CH₃ | (CH₂)₄ | 5-CH₃ | 1 |
| (CH₂)₂CH₃ | (CH₂)₄ | 5-CH₃ | 1 |
| CH₂CH₃ | (CH₂)₄ | 5-C₂H₅ | 1 |
| (CH₂)₂CH₃ | (CH₂)₄ | 5-C₂H₅ | 1 |
| CH₂CH₃ | (CH₂)₅ | — | 0 |
| (CH₂)₂CH₃ | (CH₂)₅ | — | 0 |
| CH₂CH₃ | (CH₂)₅ | 5-Cl | 1 |
| (CH₂)₂CH₃ | (CH₂)₅ | 5-Cl | 1 |
| CH₂CH₃ | (CH₂)₅ | 5-CH₃ | 1 |
| (CH₂)₂CH₃ | (CH₂)₅ | 5-CH₃ | 1 |
| CH₂CH₃ | (CH₂)₅ | 5-C₂H₅ | 1 |
| (CH₂)₂CH₃ | (CH₂)₅ | 5-C₂H₅ | 1 |
| CH₂CH₃ | (CH₂)₆ | — | 0 |
| (CH₂)₂CH₃ | (CH₂)₆ | — | 0 |
| CH₂CH₃ | (CH₂)₆ | 5-Cl | 1 |
| (CH₂)₂CH₃ | (CH₂)₆ | 5-Cl | 1 |
| CH₂CH₃ | (CH₂)₆ | 5-CH₃ | 1 |
| (CH₂)₂CH₃ | (CH₂)₆ | 5-CH₃ | 1 |
| CH₂CH₃ | (CH₂)₆ | 5-C₂H₅ | 1 |
| (CH₂)₂CH₃ | (CH₂)₆ | 5-C₂H₅ | 1 |
| CH₂CH₃ | CH₂CH=CH | — | 0 |
| (CH₂)₂CH₃ | CH₂CH=CH | — | 0 |
| CH₂CH₃ | CH₂CH=CH | 5-Cl | 0 |
| (CH₂)₂CH₃ | CH₂CH=CH | 5-Cl | 1 |
| CH₂CH₃ | CH₂CH=CH | 5-CH₃ | 1 |
| (CH₂)₂CH₃ | CH₂CH=CH | 5-CH₃ | 1 |
| CH₂CH₃ | CH₂CH=CH | 5-C₂H₅ | 1 |
| (CH₂)₂CH₃ | CH₂CH=CH | 5-C₂H₅ | 1 |
| CH₂CH₃ | CH₂CH=CHCH₂ | — | 0 |
| (CH₂)₂CH₃ | CH₂CH=CHCH₂ | — | 0 |
| CH₂CH₃ | CH₂CH=CHCH₂ | 5-Cl | 1 |
| (CH₂)₂CH₃ | CH₂CH=CHCH₂ | 5-Cl | 1 |
| CH₂CH₃ | CH₂CH=CHCH₂ | 5-CH₃ | 1 |
| (CH₂)₂CH₃ | CH₂CH=CHCH₂ | 5-CH₃ | 1 |
| CH₂CH₃ | CH₂CH=CHCH₂ | 5-C₂H₅ | 1 |
| (CH₂)₂CH₃ | CH₂CH=CHCH₂ | 5-C₂H₅ | 1 |
| CH₂CH₃ | CH₂CH₂CH=CH | — | 0 |
| (CH₂)₂CH₃ | CH₂CH₂CH=CH | — | 0 |
| CH₂CH₃ | CH₂CH₂CH=CH | 5-Cl | 1 |
| (CH₂)₂CH₃ | CH₂CH₂CH=CH | 5-Cl | 1 |
| CH₂CH₃ | CH₂CH₂CH=CH | 5-CH₃ | 1 |
| (CH₂)₂CH₃ | CH₂CH₂CH=CH | 5-CH₃ | 1 |
| CH₂CH₃ | CH₂CH₂CH=CH | 5-C₂H₅ | 1 |
| (CH₂)₂CH₃ | CH₂CH₂CH=CH | 5-C₂H₅ | 1 |
| CH₂CH₃ | (CH₂)₃CH=CH | — | 0 |
| (CH₂)₂CH₃ | (CH₂)₃CH=CH | — | 0 |
| CH₂CH₃ | (CH₂)₃CH=CH | 5-Cl | 1 |
| (CH₂)₂CH₃ | (CH₂)₃CH=CH | 5-Cl | 1 |
| CH₂CH₃ | (CH₂)₃CH=CH | 5-CH₃ | 1 |
| (CH₂)₂CH₃ | (CH₂)₃CH=CH | 5-CH₃ | 1 |
| CH₂CH₃ | (CH₂)₃CH=CH | 5-C₂H₅ | 1 |
| (CH₂)₂CH₃ | (CH₂)₃CH=CH | 5-C₂H₅ | 1 |
| CH₂CH₃ | (CH₂)₄CH=CH | — | 0 |
| (CH₂)₂CH₃ | (CH₂)₄CH=CH | — | 0 |
| CH₂CH₃ | (CH₂)₄CH=CH | 5-Cl | 1 |
| (CH₂)₂CH₃ | (CH₂)₄CH=CH | 5-Cl | 1 |
| CH₂CH₃ | (CH₂)₄CH=CH | 5-CH₃ | 1 |

TABLE A-continued

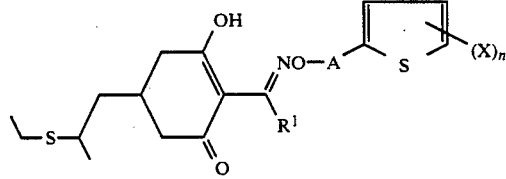

| R¹ | A | X | n |
|---|---|---|---|
| (CH₂)₂CH₃ | (CH₂)₄CH=CH | 5-CH₃ | 1 |
| CH₂CH₃ | (CH₂)₄CH=CH | 5-C₂H₅ | 1 |
| (CH₂)₂CH₃ | (CH₂)₄CH=CH | 5-C₂H₅ | 1 |

TABLE B

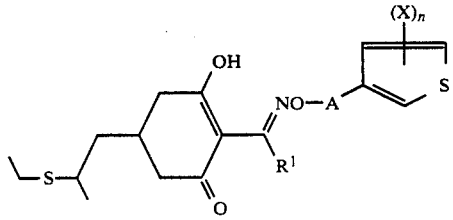

| R¹ | A | X | n |
|---|---|---|---|
| CH₂CH₃ | (CH₂)₂ | — | 0 |
| (CH₂)₂CH₃ | (CH₂)₂ | — | 0 |
| CH₂CH₃ | (CH₂)₂ | 2-Cl | 1 |
| (CH₂)₂CH₃ | (CH₂)₂ | 2-Cl | 1 |
| CH₂CH₃ | (CH₂)₂ | 5-Cl | 1 |
| (CH₂)₂CH₃ | (CH₂)₂ | 5-Cl | 1 |
| CH₂CH₃ | (CH₂)₃ | — | 0 |
| (CH₂)₂CH₃ | (CH₂)₃ | — | 0 |
| CH₂CH₃ | (CH₂)₃ | 2-Cl | 1 |
| (CH₂)₂CH₃ | (CH₂)₃ | 2-Cl | 1 |
| CH₂CH₃ | (CH₂)₃ | 5-Cl | 1 |
| (CH₂)₂CH₃ | (CH₂)₃ | 5-Cl | 1 |
| CH₂CH₃ | (CH₂)₄ | — | 0 |
| (CH₂)₂CH₃ | (CH₂)₄ | — | 0 |
| CH₂CH₃ | (CH₂)₄ | 2-Cl | 1 |
| (CH₂)₂CH₃ | (CH₂)₄ | 2-Cl | 1 |
| CH₂CH₃ | (CH₂)₄ | 5-Cl | 1 |
| (CH₂)₂CH₃ | (CH₂)₄ | 5-Cl | 1 |
| CH₂CH₃ | (CH₂)₅ | — | 0 |
| (CH₂)₂CH₃ | (CH₂)₅ | — | 0 |
| CH₂CH₃ | (CH₂)₅ | 2-Cl | 1 |
| (CH₂)₂CH₃ | (CH₂)₅ | 2-Cl | 1 |
| CH₂CH₃ | (CH₂)₅ | 5-Cl | 1 |
| (CH₂)₂CH₃ | (CH₂)₅ | 5-Cl | 1 |
| CH₂CH₃ | (CH₂)₆ | — | 0 |
| (CH₂)₂CH₃ | (CH₂)₆ | — | 0 |
| CH₂CH₃ | (CH₂)₆ | 2-Cl | 1 |
| (CH₂)₂CH₃ | (CH₂)₆ | 2-Cl | 1 |
| CH₂CH₃ | (CH₂)₆ | 5-Cl | 1 |
| (CH₂)₂CH₃ | (CH₂)₆ | 5-Cl | 1 |
| CH₂CH₃ | CH₂CH=CH | — | 0 |
| (CH₂)₂CH₃ | CH₂CH=CH | — | 0 |
| CH₂CH₃ | CH₂CH=CH | 2-Cl | 1 |
| (CH₂)₂CH₃ | CH₂CH=CH | 2-Cl | 1 |
| CH₂CH₃ | CH₂CH=CH | 5-Cl | 1 |
| (CH₂)₂CH₃ | CH₂CH=CH | 5-Cl | 1 |
| CH₂CH₃ | CH₂CH=CHCH₂ | — | 0 |
| (CH₂)₂CH₃ | CH₂CH=CHCH₂ | — | 0 |
| CH₂CH₃ | CH₂CH=CHCH₂ | 2-Cl | 1 |
| (CH₂)₂CH₃ | CH₂CH=CHCH₂ | 2-Cl | 1 |
| CH₂CH₃ | CH₂CH=CHCH₂ | 5-Cl | 1 |
| (CH₂)₂CH₃ | CH₂CH=CHCH₂ | 5-Cl | 1 |
| CH₂CH₃ | CH₂CH₂CH=CH | — | 0 |
| (CH₂)₂CH₃ | CH₂CH₂CH=CH | — | 0 |
| CH₂CH₃ | CH₂CH₂CH=CH | 2-Cl | 1 |
| (CH₂)₂CH₃ | CH₂CH₂CH=CH | 2-Cl | 1 |
| CH₂CH₃ | CH₂CH₂CH=CH | 5-Cl | 1 |
| (CH₂)₂CH₃ | CH₂CH₂CH=CH | 5-Cl | 1 |
| CH₂CH₃ | (CH₂)₃CH=CH | — | 0 |
| (CH₂)₂CH₃ | (CH₂)₃CH=CH | — | 0 |
| CH₂CH₃ | (CH₂)₃CH=CH | 2-Cl | 1 |
| (CH₂)₂CH₃ | (CH₂)₃CH=CH | 2-Cl | 1 |

TABLE B-continued

| R¹ | A | X | n |
|---|---|---|---|
| CH₂CH₃ | (CH₂)₃CH=CH | 5-Cl | 1 |
| (CH₂)₂CH₃ | (CH₂)₃CH=CH | 5-Cl | 1 |
| CH₂CH₃ | (CH₂)₄CH=CH | — | 0 |
| (CH₂)₂CH₃ | (CH₂)₄CH=CH | — | 0 |
| CH₂CH₃ | (CH₂)₄CH=CH | 2-Cl | 1 |
| (CH₂)₂CH₃ | (CH₂)₄CH=CH | 2-Cl | 1 |
| CH₂CH₃ | (CH₂)₄CH=CH | 5-Cl | 1 |
| (CH₂)₂CH₃ | (CH₂)₄CH=CH | 5-Cl | 1 |

TABLE C

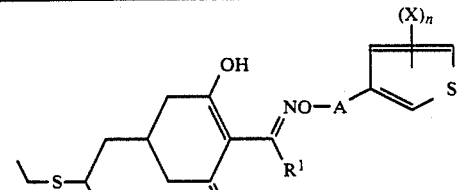

(W = Z—X_n)

| R¹ | R² | W |
|---|---|---|
| CH₂CH₃ | 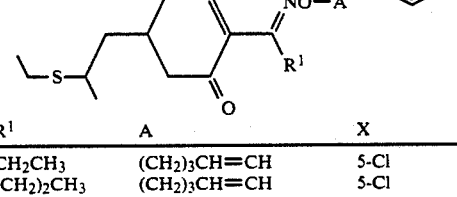 | 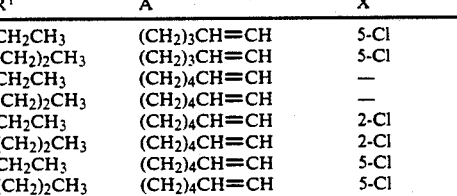 |
| (CH₂)₂CH₃ | 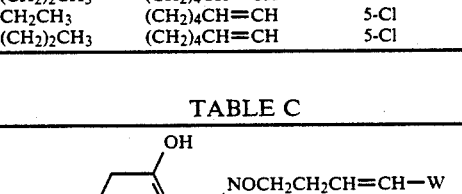 |  |
| CH₂CH₃ | 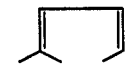 |  |
| (CH₂)₂CH₃ |  |  |
| CH₂CH₃ |  |  |
| (CH₂)₂CH₃ |  |  |
| CH₂CH₃ |  |  |
| (CH₂)₂CH₃ |  |  |
| CH₂CH₃ | 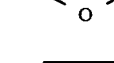 |  |

TABLE C-continued

Structure: 3-hydroxy-2-substituted cyclohex-2-enone with N-O-CH₂CH₂CH=CH-W oxime ether, R² on cyclohexenone ring, R¹ on oxime carbon.

(W = Z—Xₙ)

| R¹ | R² | W |
|---|---|---|
| (CH₂)₂CH₃ | 3-methyltetrahydrofuran-yl | 5-chlorothiophen-2-yl |
| CH₂CH₃ | 3-methyltetrahydrofuran-yl | 5-methylthiophen-2-yl |
| (CH₂)₂CH₃ | 3-methyltetrahydrofuran-yl | 5-methylthiophen-2-yl |
| CH₂CH₃ | 3-methyltetrahydrofuran-yl | 5-ethylthiophen-2-yl |
| (CH₂)₂CH₃ | 3-methyltetrahydrofuran-yl | 5-ethylthiophen-2-yl |
| CH₂CH₃ | 3-methyltetrahydrofuran-yl | thiophen-2-yl |
| (CH₂)₂CH₃ | 3-methyltetrahydrofuran-yl | thiophen-2-yl |
| CH₂CH₃ | 3-methyltetrahydrofuran-yl | 3-methyl-2-chlorothiophen-2-yl |
| (CH₂)₂CH₃ | 3-methyltetrahydrofuran-yl | 3-methyl-2-chlorothiophen-2-yl |
| CH₂CH₃ | 3-methyltetrahydrofuran-yl | 4-methyl-5-chlorothiophen-2-yl |
| (CH₂)₂CH₃ | 3-methyltetrahydrofuran-yl | 4-methyl-5-chlorothiophen-2-yl |
| CH₂CH₃ | 3-methyltetrahydrofuran-yl | 6-methylpyridin-2-yl |
| (CH₂)₂CH₃ | 3-methyltetrahydrofuran-yl | 6-methylpyridin-2-yl |
| CH₂CH₃ | 3-methyltetrahydrofuran-yl | 5-methylpyridin-3-yl |
| (CH₂)₂CH₃ | 3-methyltetrahydrofuran-yl | 5-methylpyridin-3-yl |
| CH₂CH₃ | 3-methyltetrahydrofuran-yl | 4-methylpyridin-yl |
| (CH₂)₂CH₃ | 3-methyltetrahydrofuran-yl | 4-methylpyridin-yl |
| CH₂CH₃ | 1,3-dioxolan-2-yl | furan-2-yl |
| (CH₂)₂CH₃ | 1,3-dioxolan-2-yl | furan-2-yl |
| CH₂CH₃ | 1,3-dioxolan-2-yl | 5-methylfuran-2-yl |
| (CH₂)₂CH₃ | 1,3-dioxolan-2-yl | 5-methylfuran-2-yl |
| CH₂CH₃ | 1,3-dioxolan-2-yl | 5-methylfuran-2-yl |
| (CH₂)₂CH₃ | 1,3-dioxolan-2-yl | 5-methylfuran-2-yl |
| CH₂CH₃ | 1,3-dioxolan-2-yl | 2-methylthiophen-5-yl |

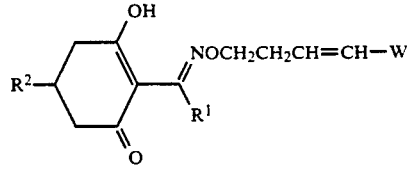

TABLE C-continued structure: cyclohexanone with OH, R², and =N-OCH₂CH₂CH=CH-W, with R¹ on the imine carbon (W = Z—Xₙ)

| R¹ | R² | W |
|---|---|---|
| (CH₂)₂CH₃ | 4-methyl-1,3-dioxolan-2-yl | thiophen-2-yl |
| CH₂CH₃ | 4-methyl-1,3-dioxolan-2-yl | 5-chlorothiophen-2-yl |
| (CH₂)₂CH₃ | 4-methyl-1,3-dioxolan-2-yl | 5-chlorothiophen-2-yl |
| CH₂CH₃ | 4-methyl-1,3-dioxolan-2-yl | 5-methylthiophen-2-yl |
| (CH₂)₂CH₃ | 4-methyl-1,3-dioxolan-2-yl | 5-methylthiophen-2-yl |
| CH₂CH₃ | 4-methyl-1,3-dioxolan-2-yl | 5-ethylthiophen-2-yl |
| (CH₂)₂CH₃ | 4-methyl-1,3-dioxolan-2-yl | 5-ethylthiophen-2-yl |
| CH₂CH₃ | 4-methyl-1,3-dioxolan-2-yl | thiophen-3-yl |
| (CH₂)₂CH₃ | 4-methyl-1,3-dioxolan-2-yl | thiophen-3-yl |
| CH₂CH₃ | 4-methyl-1,3-dioxolan-2-yl | 2-chlorothiophen-3-yl |
| (CH₂)₂CH₃ | 4-methyl-1,3-dioxolan-2-yl | 2-chlorothiophen-3-yl |
| CH₂CH₃ | 4-methyl-1,3-dioxolan-2-yl | 5-chlorothiophen-3-yl |
| (CH₂)₂CH₃ | 4-methyl-1,3-dioxolan-2-yl | 5-chlorothiophen-3-yl |

TABLE C-continued (W = Z—Xₙ)

| R¹ | R² | W |
|---|---|---|
| CH₂CH₃ | 4-methyl-1,3-dioxolan-2-yl | pyridin-2-yl |
| (CH₂)₂CH₃ | 4-methyl-1,3-dioxolan-2-yl | pyridin-2-yl |
| CH₂CH₃ | 4-methyl-1,3-dioxolan-2-yl | pyridin-3-yl |
| (CH₂)₂CH₃ | 4-methyl-1,3-dioxolan-2-yl | pyridin-3-yl |
| CH₂CH₃ | 4-methyl-1,3-dioxolan-2-yl | pyridin-3-yl |
| (CH₂)₂CH₃ | 4-methyl-1,3-dioxolan-2-yl | pyridin-4-yl |
| CH₂CH₃ | 4,5-dimethyl-1,3-dioxolan-2-yl | furan-2-yl |
| (CH₂)₂CH₃ | 4,5-dimethyl-1,3-dioxolan-2-yl | furan-2-yl |
| CH₂CH₃ | 4,5-dimethyl-1,3-dioxolan-2-yl | 5-methylfuran-2-yl |
| (CH₂)₂CH₃ | 4,5-dimethyl-1,3-dioxolan-2-yl | 5-methylfuran-2-yl |
| CH₂CH₃ | 4,5-dimethyl-1,3-dioxolan-2-yl | furan-3-yl |

TABLE C-continued

Structure: R² substituted cyclohexanedione with =N-OCH₂CH₂CH=CH-W group, OH, and R¹ substituent (see header structures).

(W = Z—Xₙ)

| R¹ | R² | W |
|---|---|---|
| (CH₂)₂CH₃ | isopropylidenedioxy-methyl (O-CH(CH₃)-CH(CH₃)-O-CH<) | furan |
| CH₂CH₃ | isopropylidenedioxy-methyl | thiophene |
| (CH₂)₂CH₃ | isopropylidenedioxy-methyl | thiophene |
| CH₂CH₃ | isopropylidenedioxy-methyl | 2-Cl-thiophene |
| (CH₂)₂CH₃ | isopropylidenedioxy-methyl | 2-Cl-thiophene |
| CH₂CH₃ | isopropylidenedioxy-methyl | 2-CH₃-thiophene |
| (CH₂)₂CH₃ | isopropylidenedioxy-methyl | 2-CH₃-thiophene |
| CH₂CH₃ | isopropylidenedioxy-methyl | 2-C₂H₅-thiophene |
| (CH₂)₂CH₃ | isopropylidenedioxy-methyl | 2-C₂H₅-thiophene |
| CH₂CH₃ | isopropylidenedioxy-methyl | thiophene |
| (CH₂)₂CH₃ | isopropylidenedioxy-methyl | thiophene |
| CH₂CH₃ | isopropylidenedioxy-methyl | 2-Cl-thiophene |
| (CH₂)₂CH₃ | isopropylidenedioxy-methyl | 2-Cl-thiophene |
| CH₂CH₃ | isopropylidenedioxy-methyl | 2-Cl-thiophene |
| (CH₂)₂CH₃ | isopropylidenedioxy-methyl | 2-Cl-thiophene |
| CH₂CH₃ | isopropylidenedioxy-methyl | 2-pyridyl |
| (CH₂)₂CH₃ | isopropylidenedioxy-methyl | 2-pyridyl |
| CH₂CH₃ | isopropylidenedioxy-methyl | 3-pyridyl |
| (CH₂)₂CH₃ | isopropylidenedioxy-methyl | 3-pyridyl |
| CH₂CH₃ | isopropylidenedioxy-methyl | 4-pyridyl |
| (CH₂)₂CH₃ | isopropylidenedioxy-methyl | 4-pyridyl |
| CH₂CH₃ | 1,3-dioxolan-2-yl | furan |
| (CH₂)₂CH₃ | 1,3-dioxolan-2-yl | furan |

TABLE C-continued structure with OH, R², R¹, NOCH₂CH₂CH=CH—W, and ketone (W = Z—X_n)

| R¹ | R² | W |
|---|---|---|
| CH₂CH₃ | 1,3-dioxolan-4-yl | 5-methylfuran-2-yl |
| (CH₂)₂CH₃ | 1,3-dioxolan-4-yl | 5-methylfuran-2-yl |
| CH₂CH₃ | 1,3-dioxolan-4-yl | furan-2-yl |
| (CH₂)₂CH₃ | 1,3-dioxolan-4-yl | furan-2-yl |
| CH₂CH₃ | 1,3-dioxolan-4-yl | thiophen-2-yl |
| (CH₂)₂CH₃ | 1,3-dioxolan-4-yl | thiophen-2-yl |
| CH₂CH₃ | 1,3-dioxolan-4-yl | 5-chlorothiophen-2-yl |
| (CH₂)₂CH₃ | 1,3-dioxolan-4-yl | 5-chlorothiophen-2-yl |
| CH₂CH₃ | 1,3-dioxolan-4-yl | 5-methylthiophen-2-yl |
| (CH₂)₂CH₃ | 1,3-dioxolan-4-yl | 5-methylthiophen-2-yl |
| CH₂CH₃ | 1,3-dioxolan-4-yl | 5-ethylthiophen-2-yl |
| (CH₂)₂CH₃ | 1,3-dioxolan-4-yl | 5-ethylthiophen-2-yl |
| CH₂CH₃ | 1,3-dioxolan-4-yl | thiophen-3-yl |

TABLE C-continued (W = Z—X_n)

| R¹ | R² | W |
|---|---|---|
| (CH₂)₂CH₃ | 1,3-dioxolan-4-yl | thiophen-3-yl |
| CH₂CH₃ | 1,3-dioxolan-4-yl | 3-chlorothiophen-2-yl |
| (CH₂)₂CH₃ | 1,3-dioxolan-4-yl | 3-chlorothiophen-2-yl |
| CH₂CH₃ | 1,3-dioxolan-4-yl | 2-chlorothiophen-3-yl |
| (CH₂)₂CH₃ | 1,3-dioxolan-4-yl | 2-chlorothiophen-3-yl |
| CH₂CH₃ | 1,3-dioxolan-4-yl | pyridin-2-yl |
| (CH₂)₂CH₃ | 1,3-dioxolan-4-yl | pyridin-2-yl |
| CH₂CH₃ | 1,3-dioxolan-4-yl | pyridin-3-yl |
| (CH₂)₂CH₃ | 1,3-dioxolan-4-yl | pyridin-3-yl |
| CH₂CH₃ | 1,3-dioxolan-4-yl | pyridin-4-yl |
| (CH₂)₂CH₃ | 1,3-dioxolan-4-yl | pyridin-4-yl |

TABLE C-continued
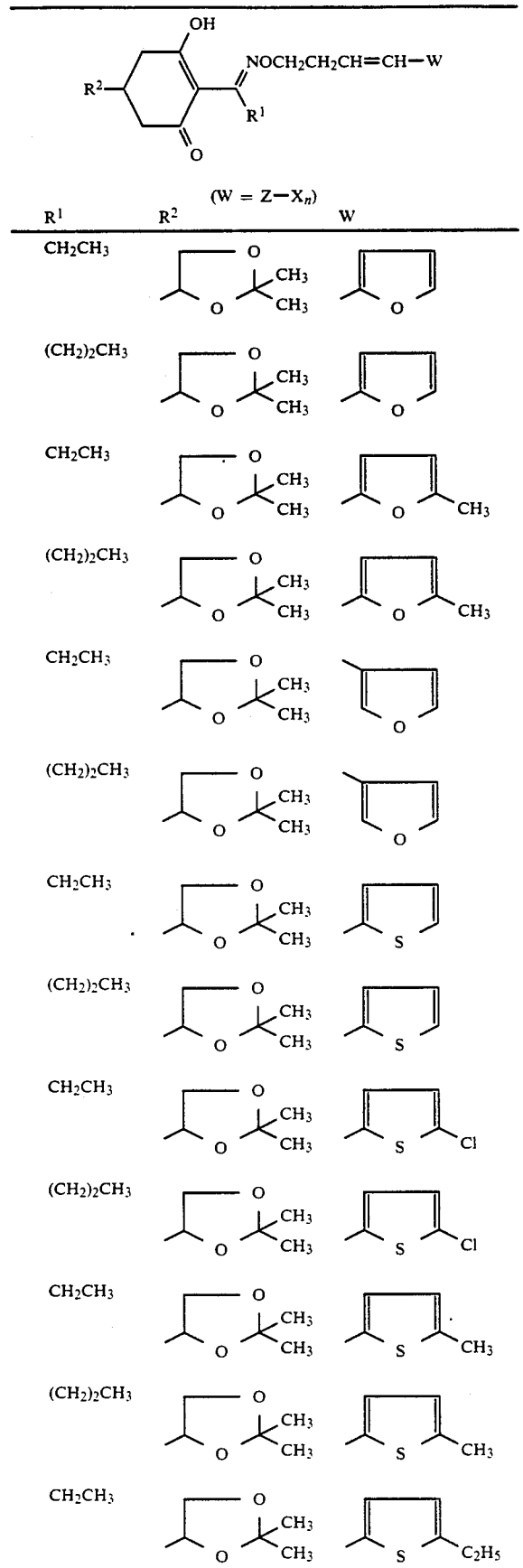
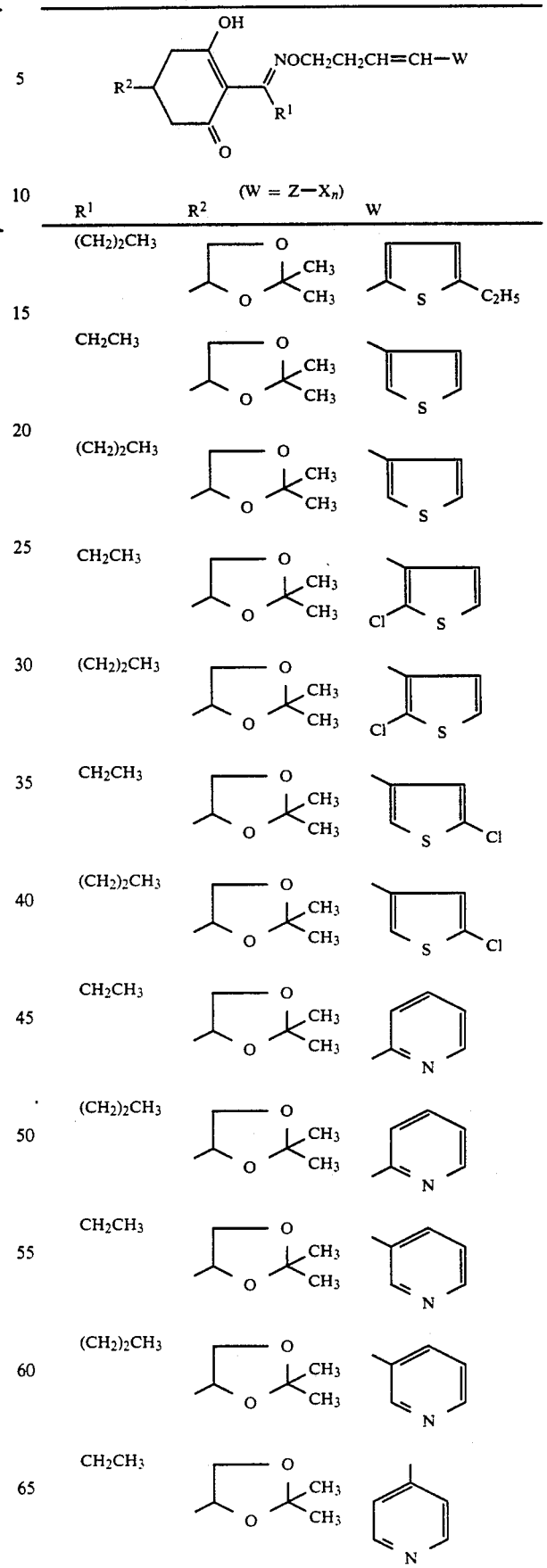

5,330,965

TABLE C-continued

Structure:

OH, NOCH₂CH₂CH=CH—W, R², R¹, with cyclohexenone core (W = Z—X$_n$)

| R¹ | R² | W |
|---|---|---|
| (CH₂)₂CH₃ | 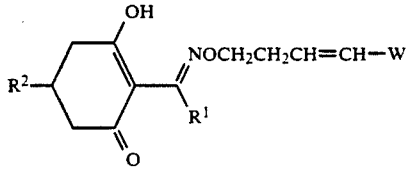 | 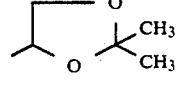 |
| CH₂CH₃ | 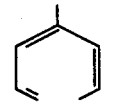 |  |
| (CH₂)₂CH₃ | 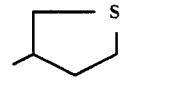 | 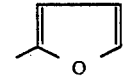 |
| CH₂CH₃ |  | 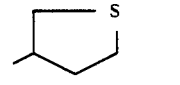 |
| (CH₂)₂CH₃ | 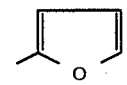 |  |
| CH₂CH₃ | 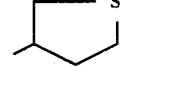 | 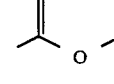 |
| (CH₂)₂CH₃ |  | 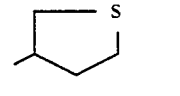 |
| CH₂CH₃ | 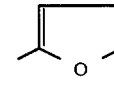 |  |
| (CH₂)₂CH₃ | 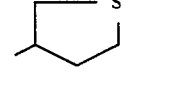 | 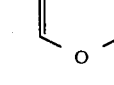 |
| CH₂CH₃ |  | 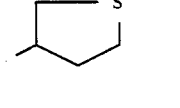 |
| (CH₂)₂CH₃ | 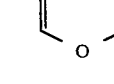 |  |
| CH₂CH₃ | 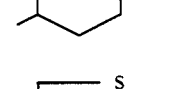 | 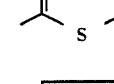 |
| (CH₂)₂CH₃ |  | 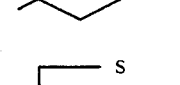 |

TABLE C-continued

Structure:

OH, NOCH₂CH₂CH=CH—W, R², R¹, with cyclohexenone core (W = Z—X$_n$)

| R¹ | R² | W |
|---|---|---|
| CH₂CH₃ | 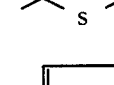 |  |
| (CH₂)₂CH₃ | 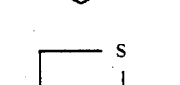 |  |
| CH₂CH₃ |  | 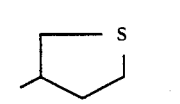 |
| (CH₂)₂CH₃ | 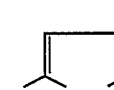 |  |
| CH₂CH₃ | 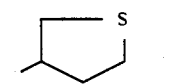 | 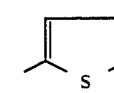 |
| (CH₂)₂CH₃ |  |  |
| CH₂CH₃ |  |  |
| (CH₂)₂CH₃ | 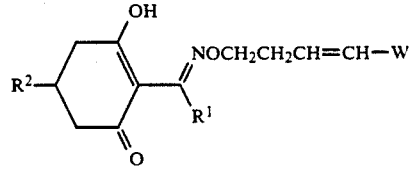 | 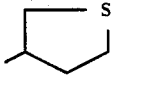 |
| CH₂CH₃ | 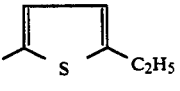 | 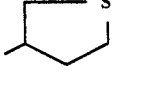 |
| (CH₂)₂CH₃ | 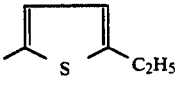 | 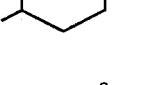 |
| CH₂CH₃ | 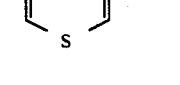 | 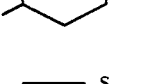 |
| (CH₂)₂CH₃ | 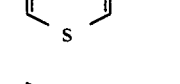 | 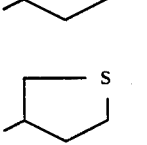 |

TABLE C-continued

Structure: cyclohexenone with OH, R², R¹, and NOCH₂CH₂CH=CH—W substituents (W = Z—X_n)

| R¹ | R² | W |
|---|---|---|
| CH₂CH₃ | 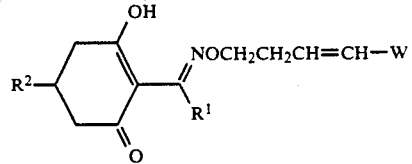 | 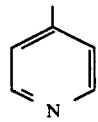 (4-pyridyl) |
| (CH₂)₂CH₃ | 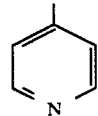 | 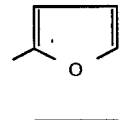 (4-pyridyl) |
| CH₂CH₃ | 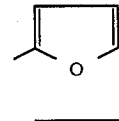 | 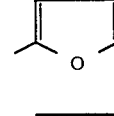 (furan) |
| (CH₂)₂CH₃ | 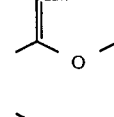 | 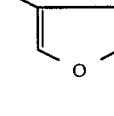 (furan) |
| CH₂CH₃ | 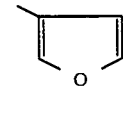 | 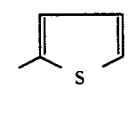 (5-methylfuran) |
| (CH₂)₂CH₃ | 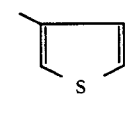 | 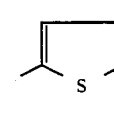 (5-methylfuran) |
| CH₂CH₃ | 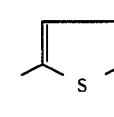 | 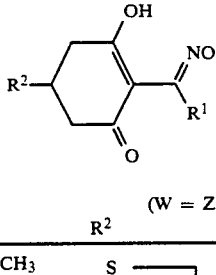 (furan) |
| (CH₂)₂CH₃ | 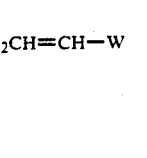 | 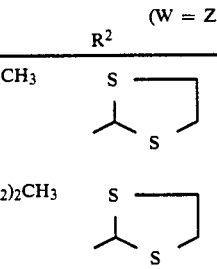 (furan) |
| CH₂CH₃ | 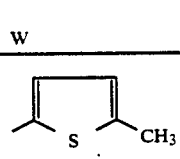 | 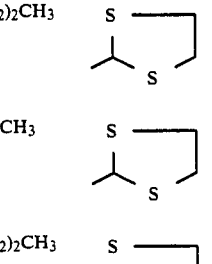 (thiophene) |
| (CH₂)₂CH₃ | 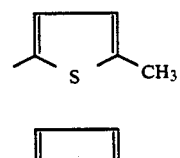 | 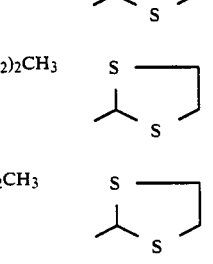 (thiophene) |
| CH₂CH₃ | 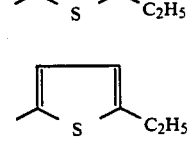 | 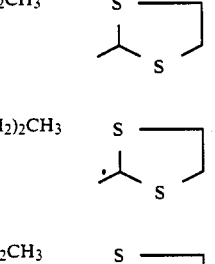 (5-Cl-thiophene) |
| (CH₂)₂CH₃ | 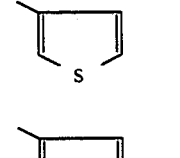 | 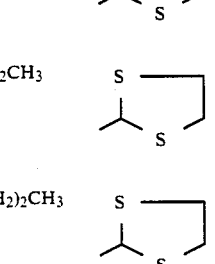 (5-Cl-thiophene) |
| CH₂CH₃ | 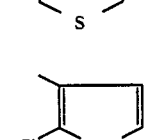 | 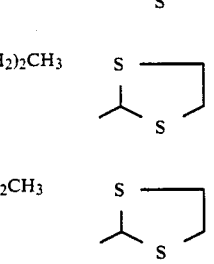 (5-methylthiophene) |
| (CH₂)₂CH₃ | 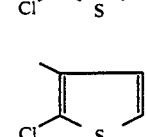 | 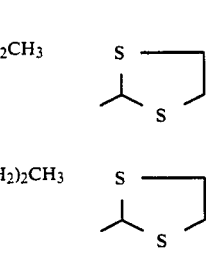 (5-methylthiophene) |
| CH₂CH₃ | 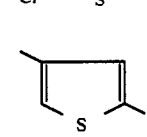 | 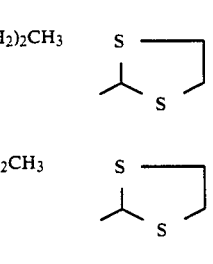 (5-ethylthiophene) |
| (CH₂)₂CH₃ | 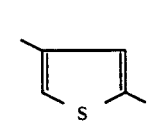 | 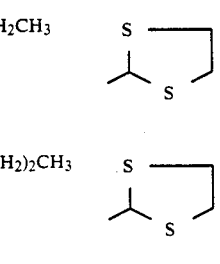 (5-ethylthiophene) |
| CH₂CH₃ | 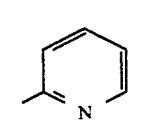 | 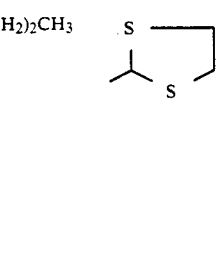 (thiophene) |
| (CH₂)₂CH₃ |  | 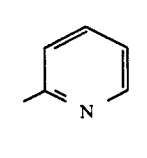 (thiophene) |
| CH₂CH₃ |  | (3-Cl-thiophene) |
| (CH₂)₂CH₃ | | (3-Cl-thiophene) |
| CH₂CH₃ | | (2-Cl-thiophene) |
| (CH₂)₂CH₃ | | (2-Cl-thiophene) |
| CH₂CH₃ | | (2-pyridyl) |
| (CH₂)₂CH₃ |  | (2-pyridyl) |

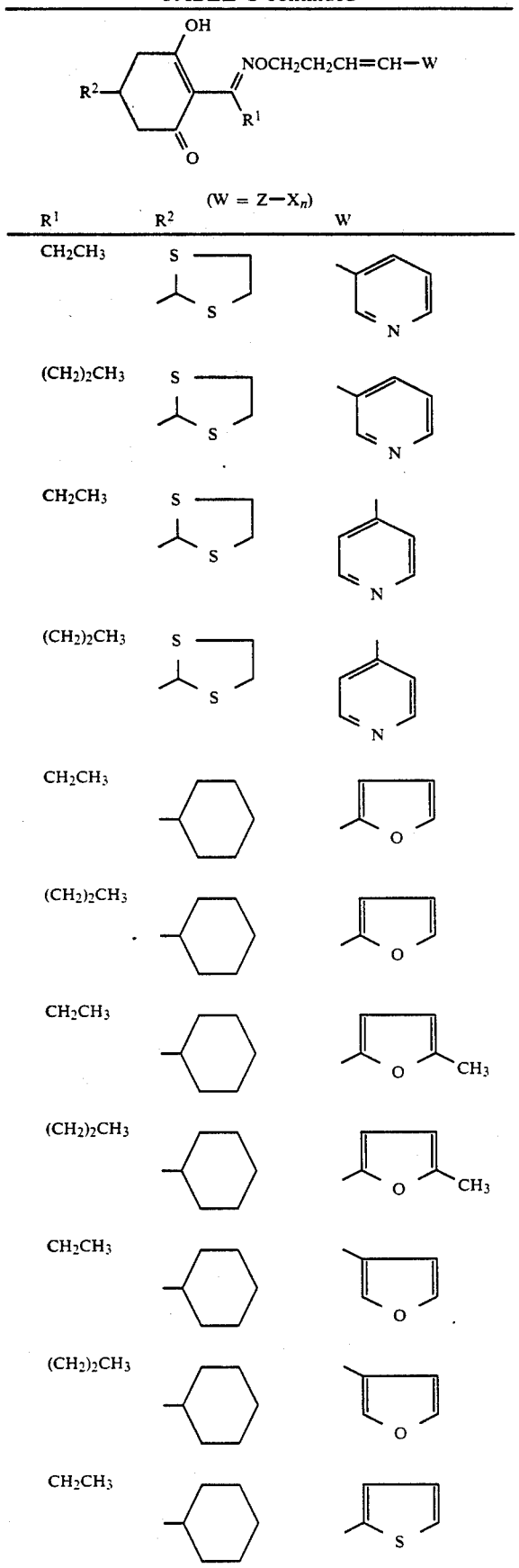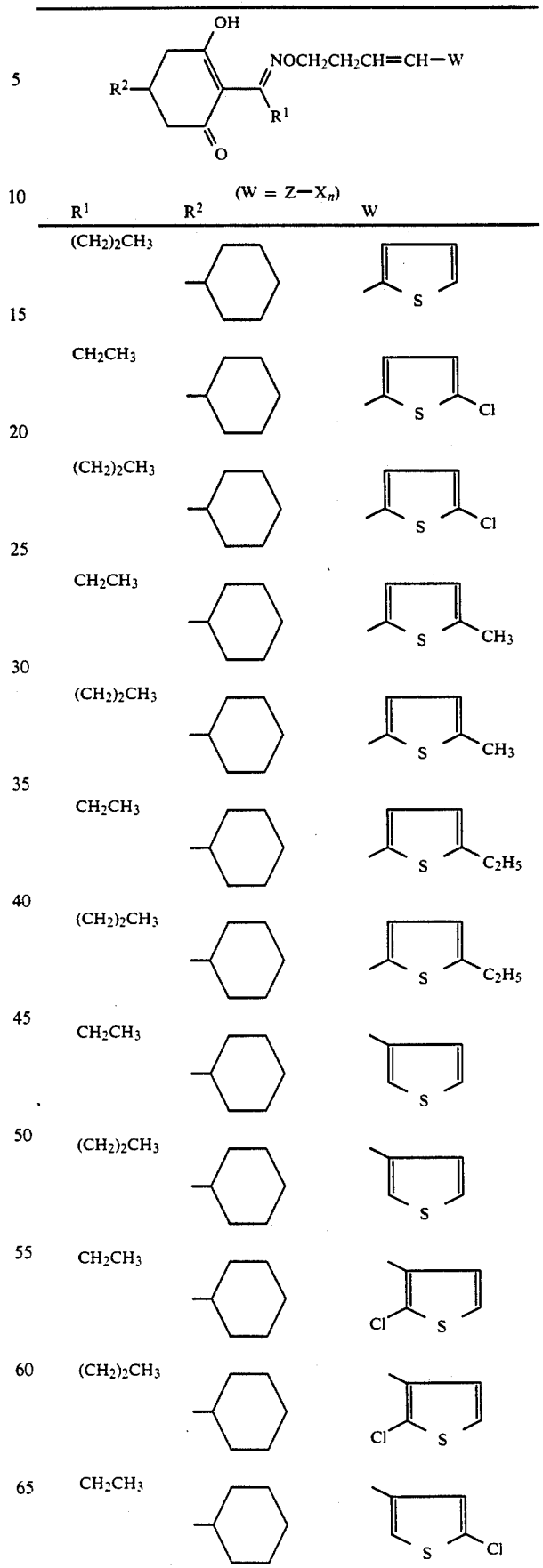

TABLE C-continued
structure
(W = Z—X_n)
| R¹ | R² | W |
|---|---|---|
| (CH₂)₂CH₃ | 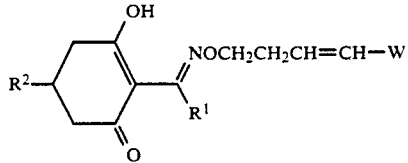 | 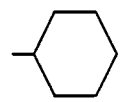 |
| CH₂CH₃ | 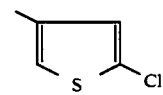 | 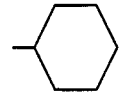 |
| (CH₂)₂CH₃ | 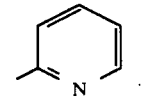 | 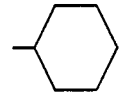 |
| CH₂CH₃ | 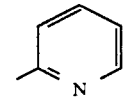 | 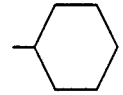 |
| (CH₂)₂CH₃ | 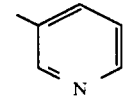 | 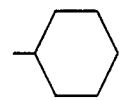 |
| CH₂CH₃ | 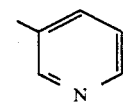 | 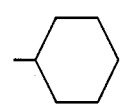 |
| (CH₂)₂CH₃ | 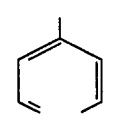 | 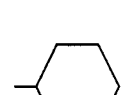 |
| CH₂CH₃ | 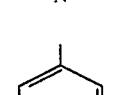 |  |
| (CH₂)₂CH₃ | 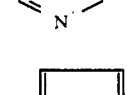 |  |
| CH₂CH₃ | 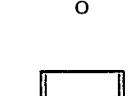 | 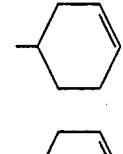 |
| (CH₂)₂CH₃ | 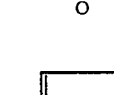 | 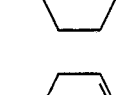 |
| CH₂CH₃ | 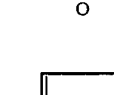 | 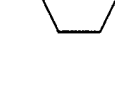 |
| (CH₂)₂CH₃ | 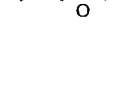 | 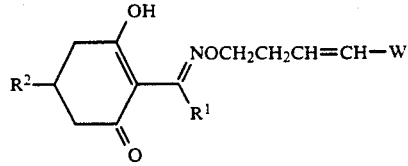 |
| CH₂CH₃ | 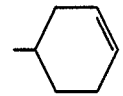 | 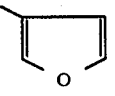 |
| (CH₂)₂CH₃ | 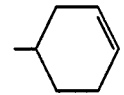 | 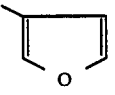 |
| CH₂CH₃ | 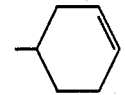 | 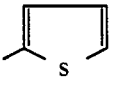 |
| (CH₂)₂CH₃ | 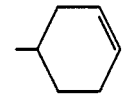 | 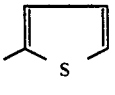 |
| CH₂CH₃ | 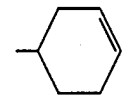 | 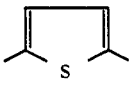 |
| (CH₂)₂CH₃ | 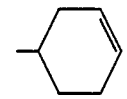 | 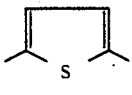 |
| CH₂CH₃ | 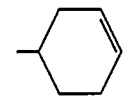 | 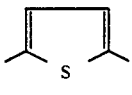 |
| (CH₂)₂CH₃ | 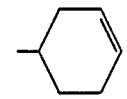 | 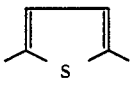 |
| CH₂CH₃ | 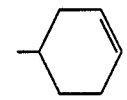 | 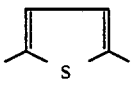 |
| (CH₂)₂CH₃ | 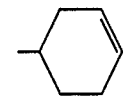 | 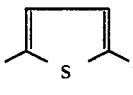 |
| CH₂CH₃ | 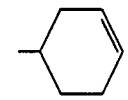 | 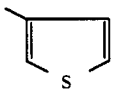 |
| (CH₂)₂CH₃ | 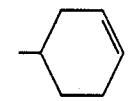 | 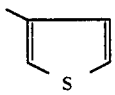 |
| CH₂CH₃ | | |
| (CH₂)₂CH₃ |  |  |

TABLE C-continued structure: cyclohexenone with OH, R², and N-OCH₂CH=CH-W oxime chain with R¹

(W = Z—Xₙ)

| R¹ | R² | W |
|---|---|---|
| CH₂CH₃ | cyclohexenyl | 3-methyl-2-chlorothiophene |
| (CH₂)₂CH₃ | cyclohexenyl | 3-methyl-2-chlorothiophene |
| CH₂CH₃ | cyclohexenyl | 4-methyl-2-chlorothiophene |
| (CH₂)₂CH₃ | cyclohexenyl | 4-methyl-2-chlorothiophene |
| CH₂CH₃ | cyclohexenyl | 2-methylpyridine |
| (CH₂)₂CH₃ | cyclohexenyl | 2-methylpyridine |
| CH₂CH₃ | cyclohexenyl | 3-methylpyridine |
| (CH₂)₂CH₃ | cyclohexenyl | 3-methylpyridine |
| CH₂CH₃ | cyclohexenyl | 4-methylpyridine |
| (CH₂)₂CH₃ | cyclohexenyl | 4-methylpyridine |
| CH₂CH₃ | dihydropyranyl | 2-methylfuran |
| (CH₂)₂CH₃ | dihydropyranyl | 2-methylfuran |
| CH₂CH₃ | dihydropyranyl | 2-methyl-5-methylfuran |
| (CH₂)₂CH₃ | dihydropyranyl | 2-methyl-5-methylfuran |
| CH₂CH₃ | dihydropyranyl | 2-methylfuran |
| (CH₂)₂CH₃ | dihydropyranyl | 2-methylfuran |
| CH₂CH₃ | dihydropyranyl | 2-methylthiophene |
| (CH₂)₂CH₃ | dihydropyranyl | 2-methylthiophene |
| CH₂CH₃ | dihydropyranyl | 2-methyl-5-chlorothiophene |
| (CH₂)₂CH₃ | dihydropyranyl | 2-methyl-5-chlorothiophene |
| CH₂CH₃ | dihydropyranyl | 2,5-dimethylthiophene |
| (CH₂)₂CH₃ | dihydropyranyl | 2,5-dimethylthiophene |

TABLE C-continued
| R¹ | R² | W |
|---|---|---|
| CH₂CH₃ | 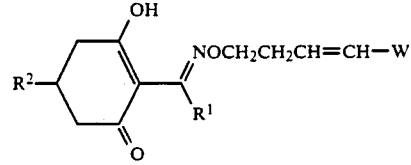 | 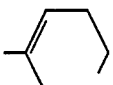 |
| (CH₂)₂CH₃ | 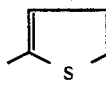 | 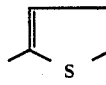 |
| CH₂CH₃ | 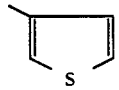 | 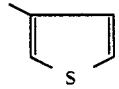 |
| (CH₂)₂CH₃ | 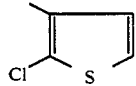 | 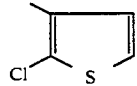 |
| CH₂CH₃ | 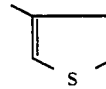 | 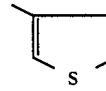 |
| (CH₂)₂CH₃ | 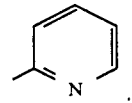 | 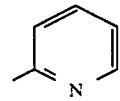 |
| CH₂CH₃ | 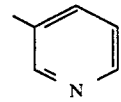 |  |
| (CH₂)₂CH₃ | 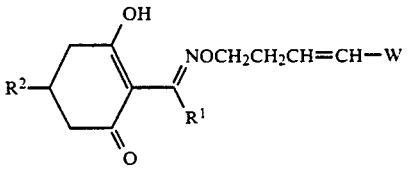 | 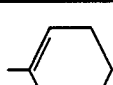 |
| CH₂CH₃ | 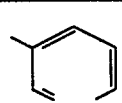 | 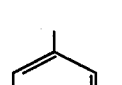 |
| (CH₂)₂CH₃ | 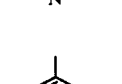 | 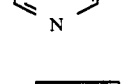 |
| CH₂CH₃ | 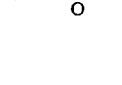 | 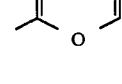 |
| (CH₂)₂CH₃ | | |
| CH₂CH₃ | | |
| (CH₂)₂CH₃ | | |
| CH₂CH₃ | | |
| (CH₂)₂CH₃ | | |
| CH₂CH₃ | | |
| (CH₂)₂CH₃ | | |

TABLE C-continued
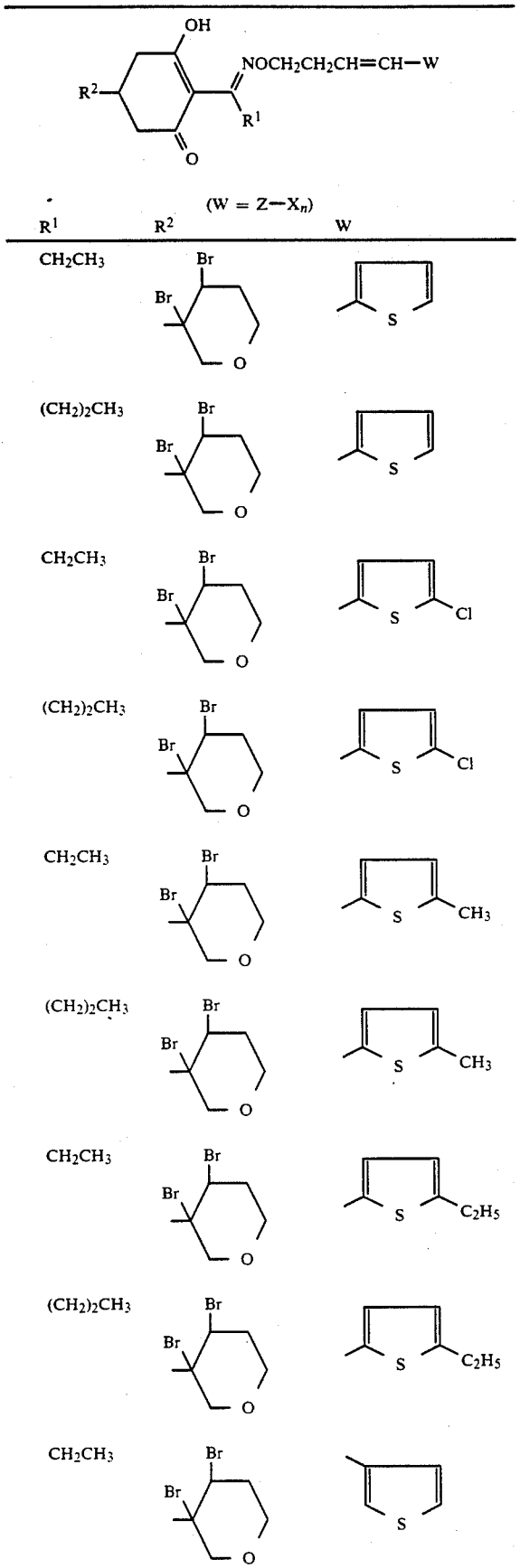
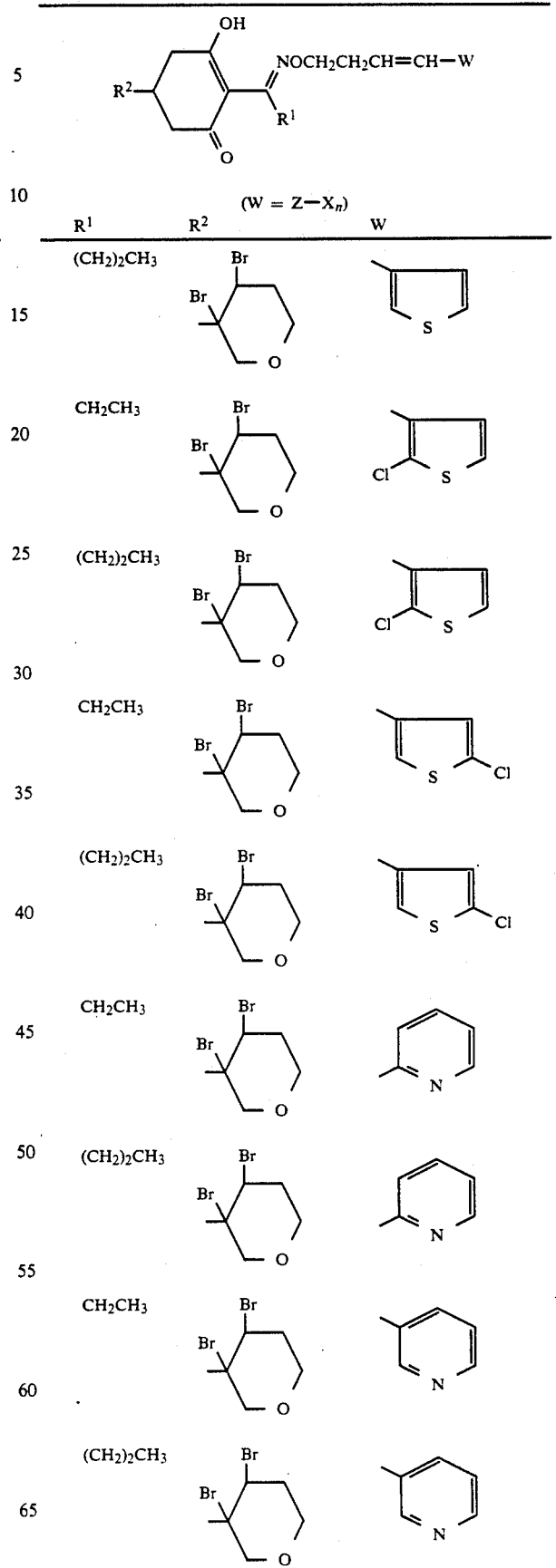

TABLE C-continued

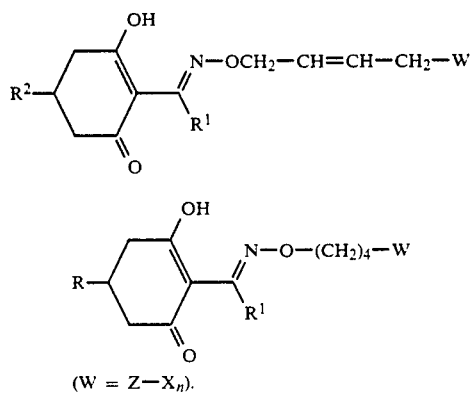

The radicals $R^1$, $R^2$ and W may be used in similar manner for the preparation of the cyclohexenone oxime ethers of the following structure types D and E

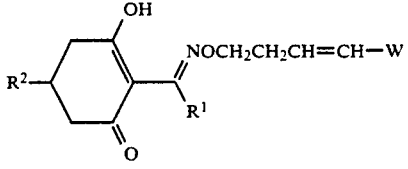

(W = Z—X$_n$).

The corresponding hydroxylamines III are also preferred.

The cyclohexenone oxime ethers I are suitable as herbicides for combating plants from the Gramineae (grasses) family.

The cyclohexenone oxime ethers I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as Kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.02 to 95, and preferably 0.5 to 90%, by weight of active ingredient. The active ingredients are used in a purity of from 90 to 100, and preferably from 95 to 100%, (according to the NMR spectrum).

Examples of formulations are as follows:

I. 90 parts by weight of compound no. 8.01 is mixed with 10 parts by weight of N-methyl-alpha-pyrrolidone. A mixture is obtained which is suitable for application in the form of very fine drops.

II. 20 parts by weight of compound no. 8.02 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 8.03 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 8.04 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 8.05 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 8.06 is intimately mixed with 97 parts by weight of particulate kaolin. A dust is obtained containing 3% by weight of the active ingredient.

VII. 30 parts by weight of compound no. 8.07 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 8.08 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may be applied pre- or post-emergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates depend on the time of the year, the plants to be combated and their growth stage, and vary from 0.001 to 3, and are preferably from 0.01 to 2.0, kg/ha.

In view of the spectrum of weeds which can be combated, the tolerance of the active ingredients by crop plants, the desired influence on growth, and in view of the numerous application methods possible, the compounds according to the invention may be used in a large number of crops. Those which follow are given by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rapeseed |
| Brassica napus var. napobrassica | swedes |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass |
| Daucus carota | carrots |
| Elais guineensis | oil palms |
| Fragaria vesca | strawberries |
| Glycine max | soybeans |
| Gossypium hirsutum (Gossypium arboreum, Gossypium herbaceum, Gossypium vitifolium) | cotton |
| Helianthus annuus | sunflowers |
| Helianthus tuberosus | Jerusalem artichoke |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicotiana tabacum (N. rustica) | tobacco |
| Olea europaea | olive trees |
| Oryza sativa | rice |
| Panicum miliaceum | millet |
| Phaseolus lunatus | limabeans |
| Phaseolus mungo | mungeans |
| Phaseolus vulgaris | snapbeans, green beans, dry beans |
| Pennisetum glaucum | pearl millet |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |

| Botanical name | Common name |
| --- | --- |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the cyclohexenone derivatives I may be mixed with each other, or mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexene-1,3-dione derivatives, quinolinecarboxylic acids, (hetero)-aryloxyphenoxypropionic acids and salts, esters, amides thereof, etc.

It may also be useful to apply the cyclohexenone derivatives I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

The directions given in the synthesis examples below were employed, after appropriate modification of the starting materials, to obtain further hydroxylamines of the formula III and cyclohexenone oxime ethers of the formula I; the compounds obtained are listed with their physical details in the tables which follow.

Example illustrating the synthesis of hydroxylamines III (E)-4-Bromo-1-(2-thienyl)-1-butene At 5° to 10° C., 225 g (1.46 mol) of cyclopropyl-2-thienylcarbinol was dripped over a period of 1 hour into 972 ml of 48% strength hydrobromic acid. The mixture was kept for 2 hours at room temperature, after which the organic phase was separated off and the aqueous solution was extracted three times, each time with 300 ml of dichloromethane. The combined organic phases were washed neutral with dilute sodium hydroxide solution and water, dried over magnesium sulfate and evaporated down under reduced pressure. There was obtained 322 g (94%, corrected) of crude bromide (GC: 92%). $^1$H-NMR (250 MHZ, CDCl$_3$): $\delta$=2.65–2.80 (m, 2H), 3.46 (t,2H), 5.90–6.10 (m, 1H), 6.61 (d, 1H), 6.80–7.00 (m, 2H), 7.14 (d, 1H).

N-[(E)-4-(2-thienyl)-3-butenyloxy]-phthalimide

At 20° to 25° C., 190 ml (1.37 mol) of triethylamine was dripped over a period of 2.5 hours into a mixture of 283 g (1.30 mol) of the bromide prepared above, 1300 ml of N-methyl-2-pyrrolidone, 10 g of potassium iodide and 212 g (1.30 mol) of N-hydroxyphthalimide. After the mixture had been kept for 4 hours at 20° to 25° C., it was poured into 4000 ml of ice water, and 500 ml of 10% strength sodium hydroxide solution was added in portions. The mixture was extracted four times, each time with 500 ml of ethyl acetate. The combined ethyl acetate phases were washed neutral with dilute sodium hydroxide solution and water, dried over magnesium sulfate and evaporated down under reduced pressure. The crude product was purified chromatographically using 1000 g of silica gel/column 30–15 cm (developer: n-hexane/dichloromethane 7:3). There was obtained 113 g (29%) of phthalimide imide ether of melting point 69°–271° C. (isopropanol). $^1$H-NMR (250 MHZ, d$_6$-DMSO): $\delta$=2.55–2.70 (m, 2H), 4.28 (t, 2H), 6.00–6.20 (m, 1H), 6.77 (d, $^1$H), 7.00 (m, 2H), 7.35 (m, 1H), 7.87 (s, 4H).

O[(E)-4-(2-thienyl)-3-butenyl]-hydroxylamine

A mixture of 90.2 g (0.30 mol) of the phthalimide ether prepared above and 136 ml of ethanolamine was stirred at 60° C. for 3 hours. The cold reaction mixture was poured into 200 ml of ice water. 200 ml of saturated sodium chloride solution was added and the hydrolysate was extracted three times, each time with 300 ml of dichloromethane. The combined organic phases were washed three times, each time with 100 ml of saturated sodium chloride solution, dried over magnesium sulfate and evaporated down under reduced pressure. There was obtained 45 g (89%) of hydroxylamine. $^1$H-NMR(250 MHz, CDCl$_3$): $\delta$=2.40–2.55 (m, 2H); 3.78 (t, 2H), 5.40 (bs, 2H), 5.95–6.20 (m, 1H), 6.57 (d, 1H), 6.80–7.15 (m, 3H).

Example illustrating the synthesis of the cyclohexenone oxime ether derivatives I 2-[1-[[(E)-4-(2-Thienyl)-3-butenyloxy]imino]-butyl]-3-hydroxy-5-(2H-tetrahydropyran-4-yl)-2-cyclohexen-1-one A mixture of 35 g (0.13 mol) of 2-butyryl-3-hydroxy-5-(2H-tetrahydropyran-4-yl)-2-cyclohexen-1-one and 24 g (0.14 mol) of O-[(E)-4-(2-thienyl)-3-butenyl]hydroxylamine in 300 ml of methanol was stirred for 16 hours. The mixture was evaporated down under reduced pressure, and the residue was taken up in 1000 ml of 10% strength sodium hydroxide solution. After extraction three times with methylene chloride, 200. ml each time, the aqueous phase was adjusted, with ice cooling, to a pH of 1 with concentrated hydrochloric acid. The aqueous phase was then extracted three times with ether, 200 ml each time, dried over magnesium sulfate and evaporated down under reduced pressure. The crude product was chromatographed using 1000 g of silica gel/column 30–15 cm (developer: ethyl acetate). There was obtained 46 g (85%) of cyclohexenone oxime ether. $^1$H-NMR(200 MHz, CDCl$_3$):$\delta$=0.95 (t, 3H), 1.17–1.96 (m, 9H), 2.13 (m, 1H), 2.36 (m, 1H), 2.43–2.70 (m, 3H), 2.88 (m, 2H), 3.36 (t, 2H), 4.02 (d, 2H), 4.15 (t, 2H), 6.00 (dt, 1H), 6.60 (d, 1H), 6.80–7.20 (m, 3H), 14.75 (s, 1H).

TABLE 1

$H_2N-O-A-Z-X_n$   III

| No. | A | Z | X | n | Phys. data NMR data in ppm |
|---|---|---|---|---|---|
| 1.01 | $CH_2CH_2$ | Thien-2-yl | — | 0 | |
| 1.02 | $CH_2CH_2$ | Pyrid-2-yl | — | 0 | |
| 1.03 | $CH_2CH_2CH_2$ | Furan-2-yl | — | 0 | 1.80–2.00 (m, 2H), 2.69 (t, 2H), 3.70 (t, 2H), 5.35 (bs, 2H) 6.00 (d, 1H), 6.27 (m, 1H), 7.30 (s, 1H), |
| 1.04 | $CH_2CH_2CH_2$ | Thien-2-yl | — | 0 | 1.85–2.00 (m, 2H), 2.87 (t, 2H), 3.68 (t, 2H), 5.30 (bs, 2H), 6.75–7.15 (m, 3H) |
| 1.05 | $CH_2CH_2CH_2$ | Thien-3-yl | — | 0 | |
| 1.06 | $CH_2CH_2CH_2$ | Pyrrol-2-yl | 1-$CH_3$ | 1 | 3.50 (s, 3H), 5.95 (m, 1H), 6.03 (m, 1H), 6.55 (m, 1H) |
| 1.07 | $CH_2CH(CH_3)CH_2$ | Thien-2-yl | — | 0 | |
| 1.08 | $CH_2CH(CH_3)CH_2$ | Thien-3-yl | — | 0 | |
| 1.09 | $CH_2CH(CH_3)CH_2$ | Thien-2-yl | 5-$CH_3$ | 1 | |
| 1.10 | $CH_2CH=CH$ | Furan-2-yl | — | 0 | |
| 1.11 | $CH_2CH=CH$ | Thien-2-yl | — | 0 | 4.32 (dd, 2H), 5.45 (bs, 2H), 6.15 (dt, 1H), 6.76 (d, 1H), 7.00 (m, 2H), 7.18 (d, 1H) |
| 1.12 | $CH_2CH=CH$ | Thien-2-yl | 5-Cl | 1 | 4.32 (dd, 2H), 5.88 (bs, 2H), 6.08 (dt, 1H), 6.63 (d, 1H), 6.72 (d, 1H), 6.77 (d, 1H) |
| 1.13 | $CH_2CH=CH$ | Thien-2-yl | 5-$CH_3$ | 1 | |
| 1.14 | $CH_2CH=CH$ | Thien-3-yl | 4-Br | 1 | |
| 1.15 | $CH_2CH=CH$ | Pyrid-3-yl | — | 0 | |
| 1.16 | $CH_2CH=CH$ | Pyrid-3-yl | — | 0 | |
| 1.17 | $CH_2C(CH_3)=CH$ | Thien-2-yl | — | 0 | |
| 1.18 | $CH_2C(CH_3)=CH$ | Thien-2-yl | 5-Cl | 1 | |
| 1.19 | $CH_2C(CH_3)=CH$ | Thien-2-yl | 5-$CH_3$ | 1 | |
| 1.20 | $CH_2C(CH_3)=CH$ | Thien-3-yl | — | 0 | |
| 1.21 | $CH_2CH_2CH_2CH_2$ | Furan-2-yl | — | 0 | 1.50–1.80 (m, 4H), 2.64 (t, 2H), 3.68 (t, 2H), 5.35 (bs, 2H), 5.97 (m, 1H), 6.18 (m, 1H), 7.30 (s, 1H) |
| 1.22 | $CH_2CH_2CH_2CH_2$ | Furan-2-yl | 5-$CH_3$ | 1 | |
| 1.23 | $CH_2CH_2CH_2CH_2$ | Thien-2-yl | — | 0 | 1.50–1.85 (m, 4H), 2.84 (t, 2H), 3.71 (t, 2H), 5.30 (bs, 2H), 6.70–7.20 (m, 3H) |
| 1.24 | $CH_2CH_2CH_2CH_2$ | Thien-2-yl | 5-$CH_3$ | 1 | 1.55–1.80 (m, 4H), 2.43 (s, 3H), 2.76 (t, 2H), 3.68 (t, 2H), 5.30 (bs, 2H), 6.54 (s, 2H) |
| 1.25 | $CH_2CH_2CH_2CH_2$ | Thien-2-yl | 5-$C_2H_5$ | 1 | 1.27 (t, 3H), 1.50–1.80 (m, 4H), 2.70–2.90 (m, 4H), 3.70 (t, 2H) 5.30 (bs, 2H), 6.77 (s, 2H) |
| 1.26 | $CH_2CH_2CH_2CH_2$ | Thien-2-yl | 5-Cl | 1 | 1.50–1.80 (m, 4H), 2.74 (t, 2H), 3.65 (t, 2H), 5.40 (bs, 2H), 6.55 (d, 1H), 6.69 (d, 1H) |
| 1.27 | $CH_2CH_2CH_2CH_2$ | Pyrrol-2-yl | 1-$CH_3$ | 1 | 3.50 (s, 3H) 5.95 (m, 1H), 6.03 (m, 1H), 6.55 (m, 1H) |
| 1.28 | $CH_2CH_2CH=CH$ | Furan-2-yl | — | 0 | 2.40–2.60 (m, 2H), 3.78 (t, 2H), 5.40 (bs, 2H), 6.00–6.50 (m, 4H), 7.30 (s, 1H) |
| 1.29 | $CH_2CH_2CH=CH$ | Furan-3-yl | — | 0 | 2.40–2.55 (m, 2H), 3.76 (t, 2H), 5.40 (bs, 2H), 5.85–6.05 (m, 1H), 6.33 (d, 1H), 6.52 (s, 1H), 7.30–7.45 (m, 2H) |
| 1.30 | $CH_2CH_2CH=CH$ | Thien-2-yl | — | 0 | 2.40–2.55 (m, 2H), 3.78 (t, 2H), 5.40 (bs, 2H), 5.95–6.20 (m, 1H), 6.57 (d, 1H), 6.80–7.15 (m, 3H) |
| 1.31 | $CH_2CH_2CH=CH$ | Thien-2-yl | 5-$CH_3$ | 1 | 2.35–2.55 (m, 5H), 3.75 (t, 2H), 5.40 (bs, 2H), 5.80–6.00 (m, 1H), 6.40–6.70 (m, 3H) |
| 1.32 | $CH_2CH_2CH=CH$ | Thien-2-yl | 5-Cl | 1 | 2.35–2.55 (m, 2H), 3.74 (t, 2H), 5.40 (bs, 2H), 5.80–6.10 (m, 1H), 6.40–6.80 (m, 3H) |
| 1.33 | $CH_2CH_2CH=CH$ | Thien-3-yl | — | 0 | 2.40–2.55 (m, 2H), 3.80 (t, 2H), 5.40 (bs, 2H), 6.00–6.15 (m, 1H), 6.48 (d, 1H), 7.00–7.30 (m, 3H) |
| 1.34 | $CH_2CH_2CH=CH$ | Thien-3-yl | 2-Cl | 1 | 2.40–2.60 (m, 2H), 3.80 (t, 2H), 5.40 (bs, 2H), 6.00–6.20 (m, 1H), 6.50 (d, 1H), 6.90–7.10 (m, 2H) |
| 1.35 | $CH_2CH_2CH=CH$ | Thien-3-yl | 5-Cl | 1 | 2.18–2.55 (m, 2H), 3.78 (t, 2H), 5.40 (bs, 2H), 5.90–6.10 (m, 1H), 6.82 (d, 1H), 6.80–7.10 (m, 2H) |
| 1.36 | $CH_2CH_2CH=C(CH_3)$ | Thien-2-yl | — | 0 | 5.95 (m, 1H), 6.80–7.15 (m, 3H) |
| 1.37 | $CH_2CH_2CH_2CH_2CH_2$ | Furan-2-yl | — | 0 | 5.97 (m, 1H), 6.20 (m, 1H), 7.30 (s, 1H) |
| 1.38 | $CH_2CH_2CH_2CH_2CH_2$ | Thien-2-yl | — | 0 | 6.80 (m, 1H), 6.90 (m, 1H), 7.10 (m, 1H) |
| 1.39 | $CH_2CH_2CH_2CH_2CH_2$ | Pyrrol-2-yl | 1-$CH_3$ | 1 | 3.50 (s, 3H), 5.95 (m, 1H), 6.03 (m, 1H), 6.55 (m, 1H) |
| 1.40 | $CH_2CH_2CH_2CH_2CH_2CH_2$ | Furan-2-yl | — | 0 | 6.00 (m, 1H), 6.20 (m, 1H), 7.30 (s, 1H) |
| 1.41 | $CH_2CH_2CH_2CH_2CH_2CH_2$ | Thien-2-yl | — | 0 | 6.77 (m, 1H), 6.90 (m, 1H), 7.07 (m, 1H) |
| 1.42 | $CH_2CH_2CH_2CH_2CH_2CH_2$ | Pyrrol-2-yl | 1-$CH_3$ | 1 | 3.50 (s, 3H), 5.95 (m, 1H), 6.03 (m, 1H), 6.55 (m, 1H) |

TABLE 2

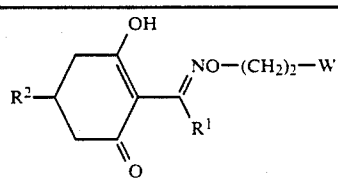

(W = $Z-X_n$)

| No. | $R^1$ | $R^2$ | W | Phys. data NMR data in ppm mp in °C. |
|---|---|---|---|---|
| 2.1 | Ethyl | Tetrahydropyran-3-yl | Furan-2-yl | |
| 2.2 | Propyl | Tetrahydropyran-3-yl | Furan-2-yl | |

TABLE 2-continued $$\text{R}^2 \diagdown \underset{\underset{O}{\parallel}}{\overset{OH}{\diagup}} \diagup \underset{R^1}{\overset{NO-(CH_2)_2-W}{\diagdown}} \quad I$$

(W = Z—X$_n$)

| No. | R$^1$ | R$^2$ | W | Phys. data NMR data in ppm mp in °C. |
|---|---|---|---|---|
| 2.3 | Ethyl | Tetrahydropyran-4-yl | Furan-2-yl | |
| 2.4 | Propyl | Tetrahydropyran-4-yl | Furan-2-yl | |
| 2.5 | Ethyl | Tetrahydrothiopyran-3-yl | Furan-2-yl | |
| 2.6 | Propyl | Tetrahydrothiopyran-3-yl | Furan-2-yl | |
| 2.7 | Ethyl | Tetrahydropyran-3-yl | Thien-2-yl | 3.92(m, 2H), 4.33(t, 2H), 6.82 (m, 1H), 6.93(m, 1H), 7.13(m, 1H) |
| 2.8 | Propyl | Tetrahydropyran-3-yl | Thien-2-yl | 3.92(m, 2H), 4.33(t, 2H), 6.82 (m, 1H), 6.93(m, 1H), 7.13(m, 1H) |
| 2.9 | Ethyl | Tetrahydropyran-4-yl | Thien-2-yl | 4.00(m, 2H), 4.33(t, 2H), 6.82 (m, 1H), 6.93(m, 1H), 7.13(m, 1H) |
| 2.10 | Propyl | Tetrahydropyran-4-yl | Thien-2-yl | 4.00(m, 2H), 4.33(t, 2H), 6.82 (m, 1H), 6.93(m, 1H), 7.13(m, 1H) |
| 2.11 | Ethyl | Tetrahydrothiopyran-3-yl | Thien-2-yl | 4.30(t, 2H), 6.82(m, 1H), 6.93(m, 1H), 7.13(m, 1H) |
| 2.12 | Propyl | Tetrahydrothiopyran-3-yl | Thien-2-yl | 4.30(t, 2H), 6.82(m, 1H), 6.93(m, 1H), 7.13(m, 1H) |
| 2.13 | Ethyl | Tetrahydropyran-3-yl | Pyrid-2-yl | 3.90(m, 2H), 4.46(t, 2H), 7.20 (m, 2H), 7.67(m, 1H), 8.50(m, 1H) |
| 2.14 | Propyl | Tetrahydropyran-3-yl | Pyrid-2-yl | |
| 2.15 | Ethyl | Tetrahydropyran-4-yl | Pyrid-2-yl | 4.00(m, 2H), 4.46(t, 2H), 7.20 (m, 2H), 7.67(m, 1H), 8.50(m, 1H) |
| 2.16 | Propyl | Tetrahydropyran-4-yl | Pyrid-2-yl | |
| 2.17 | Ethyl | Tetrahydrothiopyran-3-yl | Pyrid-2-yl | 4.46(t, 2H), 7.20(m, 2H), 7.67 (m, 1H), 8.50(m, 1H) |
| 2.18 | Ethyl | Tetrahydrothiopyran-3-yl | Pyrid-2-yl | |

TABLE 3

$$\text{R}^2 \diagdown \underset{\underset{O}{\parallel}}{\overset{OH}{\diagup}} \diagup \underset{R^1}{\overset{NO-(CH_2)_3-W}{\diagdown}} \quad I$$

(W = Z—X$_n$)

| No. | R$^1$ | R$^2$ | W | Phys. data NMR data in ppm mp in °C. |
|---|---|---|---|---|
| 3.1 | Ethyl | Tetrahydropyran-3-yl | Furan-2-yl | 3.93(m, 2H), 4.10(t, 2H), 6.00 (m, 1H), 6.26(m, 1H), 7.33(m, 1H) |
| 3.2 | Propyl | Tetrahydropyran-3-yl | Furan-2-yl | 3.93(m, 2H), 4.10(t, 2H), 6.00 (m, 1H), 6.26(m, 1H), 7.33(m, 1H) |
| 3.3 | Ethyl | Tetrahydropyran-4-yl | Furan-2-yl | 78–82 |
| 3.4 | Propyl | Tetrahydropyran-4-yl | Furan-2-yl | 48–52 |
| 3.5 | Ethyl | Tetrahydrothiopyran-3-yl | Furan-2-yl | 54–58 |
| 3.6 | Propyl | Tetrahydrothiopyran-3-yl | Furan-2-yl | 4.10(t, 2H), 6.00(m, 1H), 6.26 (m, 1H), 7.33(m, 1H) |
| 3.7 | Ethyl | Tetrahydropyran-3-yl | Thien-2-yl | 72–74 |
| 3.8 | Propyl | Tetrahydropyran-3-yl | Thien-2-yl | 3.93(m, 2H), 4.10(t, 2H), 6.82 (m, 1H), 6.93(m, 1H), 7.33(m, 1H) |
| 3.9 | Ethyl | Tetrahydropyran-4-yl | Thien-2-yl | 86–90 |
| 3.10 | Propyl | Tetrahydropyran-4-yl | Thien-2-yl | 55–58 |
| 3.11 | Ethyl | Tetrahydrothiopyran-3-yl | Thien-2-yl | 4.12(t, 2H), 6.82(m, 1H), 6.93 (m, 1H), 7.13(m, 1H), |
| 3.12 | Propyl | Tetrahydrothiopyran-3-yl | Thien-2-yl | 4.12(t, 2H), 6.82(m, 1H), 6.93 (m, 1H), 7.13(m, 1H), |
| 3.13 | Ethyl | Tetrahydropyran-3-yl | Thien-3-yl | 73–74 |
| 3.14 | Propyl | Tetrahydropyran-3-yl | Thien-3-yl | 4.05(t, 2H), 6.95(m, 2H), 7.25 (m, 1H) |
| 3.15 | Ethyl | Tetrahydropyran-4-yl | Thien-3-yl | 105–107 |
| 3.16 | Propyl | Tetrahydropyran-4-yl | Thien-3-yl | 68–70 |
| 3.17 | Ethyl | Tetrahydrothiopyran-3-yl | Thien-3-yl | 57–59 |
| 3.18 | Propyl | Tetrahydrothiopyran-3-yl | Thien-3-yl | 4.05(t, 2H), 6.95(m, 2H), 7.25 (m, 1H) |

TABLE 3-continued

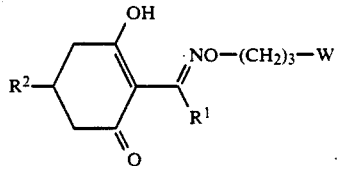

(W = Z—X$_n$)

| No. | R$^1$ | R$^2$ | W | Phys. data NMR data in ppm mp in °C. |
|---|---|---|---|---|
| 3.19 | Ethyl | Tetrahydropyran-3-yl | 1-Methylpyrrol-2-yl | 3.90(m, 2H), 4.12(t, 2H), 5.90 (m, 1H), 6.06(m, 1H), 6,53(m, 1H) |
| 3.20 | Propyl | Tetrahydropyran-3-yl | 1-Methylpyrrol-2-yl | 3.90(m, 2H), 4.12(t, 2H), 5.90 (m, 1H), 6.60(m, 1H), 6,53(m, 1H) |
| 3.21 | Ethyl | Tetrahydropyran-4-yl | 1-Methylpyrrol-2-yl | 4.00(m, 2H), 4.12(t, 2H), 5.90 (m, 1H), 6.60(m, 1H), 6,53(m, 1H) |
| 3.22 | Ethyl | Tetrahydropyran-4-yl | 1-Methylpyrrol-2-yl | 4.00(m, 2H). 4.12(t, 2H), 5.90 (m, 1H), 6.06(m, 1H), 6,53(m, 1H) |
| 3.23 | Ethyl | Tetrahydropyran-3-yl | 1-Methylpyrrol-2-yl | 4.12(t, 2H), 5.90(m, 1H), 6.06 (m, 1H), 6,53(m, 1H) |
| 3.24 | Propyl | Tetrahydropyran-3-yl | 1-Methylpyrrol-2-yl | 4.12(t, 2H), 5.90, (m, 1H), 6.06 (m, 1H), 6,53(m, 1H) |

TABLE 4

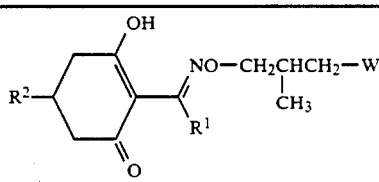

I    (W = Z—X$_n$)

| No. | R$^1$ | R$^2$ | W | Phys. data NMR data in ppm mp in °C. |
|---|---|---|---|---|
| 4.01 | Ethyl | Tetrahydropyran-3-yl | Thien-2-yl | 35 |
| 4.02 | Propyl | Tetrahydropyran-3-yl | Thien-2-yl | 6.85-7.20(m, 3H) |
| 4.03 | Ethyl | Tetrahydropyran-4-yl | Thien-2-yl | 59-61 |
| 4.04 | Propyl | Tetrahydropyran-4-yl | Thien-2-yl | 6.70-7.20(m, 3H) |
| 4.05 | Ethyl | Tetrahydrothiopyran-3-yl | Thien-2-yl | 6.70-7.20(m, 3H) |
| 4.06 | Propyl | Tetrahydrothiopyran-3-yl | Thien-2-yl | 6.70-7.20(m, 3H) |
| 4.07 | Ethyl | Tetrahydropyran-3-yl | Thien-3-yl | 38-40 |
| 4.08 | Propyl | Tetrahydropyran-3-yl | Thien-3-yl | 6.80-7.30(m, 3H) |
| 4.09 | Ethyl | Tetrahydropyran-4-yl | Thien-3-yl | 58-60 |
| 4.10 | Propyl | Tetrahydropyran-4-yl | Thien-3-yl | 6.80-7.40(m, 3H) |
| 4.11 | Ethyl | Tetrahydrothiopyran-3-yl | Thien-3-yl | 6.90(m, 2H), 7.25(m, 1H) |
| 4.12 | Propyl | Tetrahydrothiopyran-3-yl | Thien-3-yl | 6.90(m, 2H), 7.30(m, 1H) |
| 4.13 | Ethyl | Tetrahydropyran-3-yl | 5-Methylthien-2-yl | 48-50 |
| 4.14 | Propyl | Tetrahydropyran-3-yl | 5-Methylthien-2-yl | 2.40(s, 3H), 6.55(s, 2H) |
| 4.15 | Ethyl | Tetrahydropyran-4-yl | 5-Methylthien-2-yl | 2.40(s, 3H), 6.55(s, 2H) |
| 4.16 | Propyl | Tetrahydropyran-4-yl | 5-Methylthien-2-yl | 2.40(s, 3H), 6.75(s, 2H) |
| 4.17 | Ethyl | Tetrahydrothiopyran-3-yl | 5-Methylthien-2-yl | 2.45(s, 3H), 6.75(s, 2H) |
| 4.18 | Ethyl | Tetrahydrothiopyran-3-yl | 5-Methylthien-2-yl | 56-58 |

TABLE 5

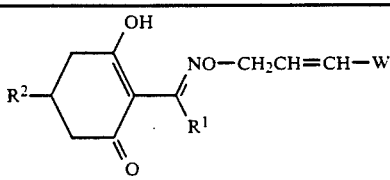

I    (W = Z—X$_n$)

| No. | R$^1$ | R$^2$ | W | Phys. data NMR data in ppm mp in °C. |
|---|---|---|---|---|
| 5.02 | Propyl | Tetrahydropyran-3-yl | Furan-2-yl | 4.70(d, 2H), 6.00–6.60(m, 4H), 7.40(s, 1H) |
| 5.03 | Ethyl | Tetrahydropyran-4-yl | Furan-2-yl | 99–100 |
| 5.04 | Propyl | Tetrahydropyran-4-yl | Furan-2-yl | 4.70(d, 2H), 6.10–6.60(m, 4H), 7.40(s, 1H) |
| 5.05 | Ethyl | Tetrahydrothiopyran-3-yl | Furan-2-yl | 4.65(d, 2H), 6.10–6.60(m, 4H), |

TABLE 5-continued

Structure: cyclohexanone with OH, R², and C(R¹)=N-O-CH₂CH=CH-W substituents; I (W = Z—X$_n$)

| No. | R¹ | R² | W | Phys. data NMR data in ppm mp in °C. |
|---|---|---|---|---|
| 5.06 | Propyl | Tetrahydrothiopyran-3-yl | Furan-2-yl | 7.40(s, 1H) 4.70(d, 2H), 6.10–6.60(m, 4H), 7.40(s, 1H) |
| 5.07 | Ethyl | Tetrahydrothiopyran-3-yl | 5-Chlorothien-2-yl | 4.60(d, 2H), 6.00(dt, 1H), 6.70(d, 1H), 6.80(m, 2H) |
| 5.08 | Propyl | Tetrahydrothiopyran-3-yl | 5-Chlorothien-2-yl | 4.60(d, 2H), 6.00(dt, 1H), 6.70(d, 1H), 6.80(m, 2H) |
| 5.09 | Ethyl | Tetrahydropyran-3-yl | Thien-2-yl | 112–114 |
| 5.10 | Propyl | Tetrahydropyran-3-yl | Thien-2-yl | 67–68 |
| 5.11 | Ethyl | Tetrahydropyran-4-yl | Thien-2-yl | 123–125 |
| 5.12 | Propyl | Tetrahydropyran-4-yl | Thien-2-yl | 70–72 |
| 5.13 | Ethyl | Tetrahydrothiopyran-3-yl | Thien-2-yl | 104–106 |
| 5.14 | Propyl | Tetrahydrothiopyran-3-yl | Thien-2-yl | 85–88 |
| 5.15 | Ethyl | 2,4,6-Trimethylphenyl | Thien-2-yl | 4.65(d, 2H), 6.10–6.30(m, 1H), 6.70–7.20(m, 6H) |
| 5.16 | Ethyl | Tetrahydropyran-3-yl | Thien-3-yl | 87–90 |
| 5.17 | Propyl | Tetrahydropyran-3-yl | Thien-3-yl | 3.90(m, 2H), 4.67(d, 2H), 6.12 (dt, 1H), 6.63(d, 1H), 7.20(m, 3H) |
| 5.18 | Ethyl | Tetrahydropyran-4-yl | Thien-3-yl | 128–135 |
| 5.19 | Propyl | Tetrahydropyran-4-yl | Thien-3-yl | 92–95 |
| 5.20 | Ethyl | Tetrahydrothiopyran-3-yl | Thien-3-yl | 79–81 |
| 5.21 | Propyl | Tetrahydrothiopyran-3-yl | Thien-3-yl | 86–92 |
| 5.22 | Ethyl | Tetrahydropyran-3-yl | 5-Methylthien-2-yl | 88–89 |
| 5.23 | Propyl | Tetrahydropyran-3-yl | 5-Methylthien-2-yl | 70–71 |
| 5.24 | Ethyl | Tetrahydropyran-4-yl | 5-Methylthien-2-yl | 108–110 |
| 5.25 | Propyl | Tetrahydropyran-4-yl | 5-Methylthien-2-yl | 104–105 |
| 5.26 | Ethyl | Tetrahydrothiopyran-3-yl | 5-Methylthien-2-yl | 111–112 |
| 5.27 | Propyl | Tetrahydrothiopyran-3-yl | 5-Methylthien-2-yl | 75–77 |
| 5.28 | Ethyl | Tetrahydropyran-3-yl | 4-Bromothien-2-yl | 78–80 |
| 5.29 | Propyl | Tetrahydropyran-3-yl | 4-Bromothien-2-yl | 6.70(d, 1H), 6.95(s, 1H), 7.05 (s, 1H) |
| 5.30 | Ethyl | Tetrahydroypyran-4-yl | 4-Bromothien-2-yl | 122–124 |
| 5.31 | Propyl | Tetrahydroypyran-4-yl | 4-Bromothien-2-yl | 88–90 |
| 5.32 | Ethyl | Tetrahydrothiopyran-3-yl | 4-Bromothien-2-yl | 72–74 |
| 5.33 | Propyl | Tetrahydrothiopyran-3-yl | 4-Bromothien-2-yl | 6.70(d, 1H), 6.90(s, 1H), 7.05 (s, 1H) |
| 5.34 | Ethyl | Tetrahydropyran-3-yl | Pyrid-3-yl | 146–148 |
| 5.35 | Propyl | Tetrahydropyran-3-yl | Pyrid-3-yl | 6.40(dt, 1H), 7.30, 7.75, 8.40–8.70(3m, 4H) |
| 5.36 | Ethyl | Tetrahydropyran-4-yl | Pyrid-3-yl | 164–165 |
| 5.37 | Propyl | Tetrahydropyran-4-yl | Pyrid-3-yl | 73–78 |
| 5.38 | Ethyl | Tetrahydrothiopyran-3-yl | Pyrid-3-yl | 6.40(dt, 1H), 7.30, 7.75, 8.40–8.70(3m, 4H) |
| 5.39 | Propyl | Tetrahydrothiopyran-3-yl | Pyrid-3-yl | 6.40(dt, 1H), 7.30, 7.75, 8.40–8.70(3m, 4H) |

TABLE 6

Structure: cyclohexanone with OH, R², and C(R¹)=N-O-CH₂C(CH₃)=CH-W substituents; I (W = Z—X$_n$)

| No. | R¹ | R² | W | Phys. data NMR data in ppm mp in °C. |
|---|---|---|---|---|
| 6.01 | Ethyl | Tetrahydropyran-3-yl | Thien-2-yl | |
| 6.02 | Propyl | Tetrahydropyran-3-yl | Thien-2-yl | |
| 6.03 | Ethyl | Tetrahydropyran-4-yl | Thien-2-yl | 97–98 |
| 6.04 | Propyl | Tetrahydropyran-4-yl | Thien-2-yl | 6.65(s, 1H), 6.90–7.30(2m, 3H), |
| 6.05 | Ethyl | Tetrahydrothiopyran-3-yl | Thien-2-yl | 88–90 |
| 6.06 | Propyl | Tetrahydrothiopyran-3-yl | Thien-2-yl | 6.65(s, 1H), 6.90–7.80(2m, 3H), |
| 6.07 | Ethyl | Tetrahydropyran-3-yl | Thien-3-yl | 6.50(s, 1H), 7.00–7.40(m, 3H) |
| 6.08 | Propyl | Tetrahydropyran-3-yl | Thien-3-yl | 6.50(s, 1H), 7.00–7.40(m, 3H) |

TABLE 6-continued

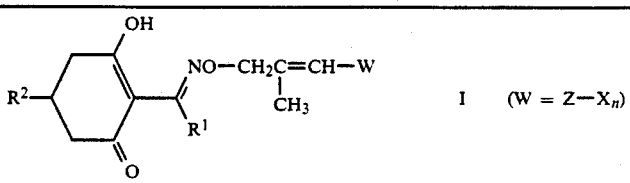

I    (W = Z—X$_n$)

| No. | R$^1$ | R$^2$ | W | Phys. data NMR data in ppm mp in °C. |
|---|---|---|---|---|
| 6.09 | Ethyl | Tetrahydropyran-4-yl | Thien-3-yl | 88–90 |
| 6.10 | Propyl | Tetrahydropyran-4-yl | Thien-3-yl | 6.55(s, 1H), 7.00–7.40(m, 3H) |
| 6.11 | Ethyl | Tetrahydrothiopyran-3-yl | Thien-3-yl | 6.55(s, 1H), 7.00–7.40(m, 3H), |
| 6.12 | Propyl | Tetrahydrothiopyran-3-yl | Thien-3-yl | 6.50(s, 1H), 7.00–7.40(m, 3H) |
| 6.13 | Ethyl | Tetrahydropyran-3-yl | 5-Methylthien-2-yl | 108–110 |
| 6.14 | Propyl | Tetrahydropyran-3-yl | 5-Methylthien-2-yl | 6.60(s, 1H), 6.65–7.00(m, 2H) |
| 6.15 | Ethyl | Tetrahydropyran-4-yl | 5-Methylthien-2-yl | 111–112 |
| 6.16 | Propyl | Tetrahydropyran-4-yl | 5-Methylthien-2-yl | 6.60(s, 1H), 6.65–7.00(m, 2H) |
| 6.17 | Ethyl | Tetrahydrothiopyran-3-yl | 5-Methylthien-2-yl | 119–120 |
| 6.18 | Propyl | Tetrahydrothiopyran-3-yl | 5-Methylthien-2-yl | 6.55(s, 1H), 6.60–7.00(m, 2H) |
| 6.19 | Ethyl | Tetrahydropyran-3-yl | 5-Chlorothien-2-yl | 82–85 |
| 6.20 | Propyl | Tetrahydropyran-3-yl | 5-Chlorothien-2-yl | 6.70(s, 1H), 6.90(m, 2H) |
| 6.21 | Ethyl | Tetrahydropyran-4-yl | 5-Chlorothien-2-yl | 124–126 |
| 6.22 | Propyl | Tetrahydropyran-4-yl | 5-Chlorothien-2-yl | 97–98 |
| 6.23 | Ethyl | Tetrahydrothiopyran-3-yl | 5-Chlorothien-2-yl | 103–105 |
| 6.24 | Propyl | Tetrahydrothiopyran-3-yl | 5-Chlorothien-2-yl | 6.65(s, 1H), 6.90(m, 2H). |

TABLE 7

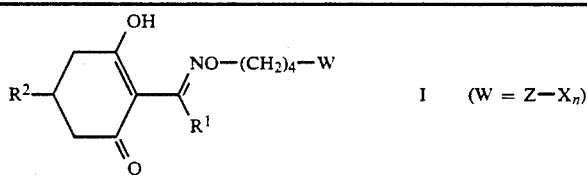

I    (W = Z—X$_n$)

| No. | R$^1$ | R$^2$ | W | Phys. data NMR data in ppm mp in °C. |
|---|---|---|---|---|
| 7.01 | Ethyl | Tetrahydropyran-3-yl | Furan-2-yl | 3.93(m, 2H), 4.07(m, 2H), 6.00 (m, 1H), 6.26(m, 1H), 7.30(m, 1H) |
| 7.02 | Propyl | Tetrahydropyran-3-yl | Furan-2-yl | 3.93(m, 2H), 4.07(m, 2H), 6.00 (m, 1H), 6.26(m, 1H), 7.30(m, 1H) |
| 7.03 | Ethyl | Tetrahydropyran-4-yl | Furan-2-yl | 3.90–4.13(m, 4H), 6.00(m, 1H), 6.26(m, 1H), 7.30(m, 1H) |
| 7.04 | Propyl | Tetrahydropyran-4-yl | Furan-2-yl | 3.90–4.13(m, 4H), 6.00(m, 1H), 6.26(m, 1H), 7.30(m, 1H) |
| 7.05 | Ethyl | Tetrahydrothiopyran-3-yl | Furan-2-yl | 4.05(m, 2H), 6.00(m, 1H), 6.26(m, 1H), 7.30(m, 1H) |
| 7.06 | Propyl | Tetrahydrothiopyran-3-yl | Furan-2-yl | 4.05(m, 2H), 6.00(m, 1H), 6.26(m, 1H), 7.30(m, 1H) |
| 7.07 | Ethyl | Tetrahydropyran-3-yl | 5-Methylfuran-2-yl | 62–64· |
| 7.08 | Propyl | Tetrahydropyran-3-yl | 5-Methylfuran-2-yl | 3.93(m, 2H), 4.07(m, 2H), 5.87 (m, 2H) |
| 7.09 | Ethyl | Tetrahydropyran-4-yl | 5-Methylfuran-2-yl | 76–78 |
| 7.10 | Propyl | Tetrahydropyran-4-yl | 5-Methylfuran-2-yl | 3.90–4.15(m, 4H), 5.87(m, 2H) |
| 7.11 | Ethyl | Tetrahydrothiopyran-3-yl | 5-Methylfuran-2-yl | 4.07(m, 2H), 5.87(m, 2H) |
| 7.12 | Propyl | Tetrahydrothiopyran-3-yl | 5-Methylfuran-2-yl | 4.07(m, 2H), 5.87(m, 2H) |
| 7.13 | Ethyl | Tetrahydropyran-3-yl | Thien-2-yl | 3.80–4.15(m, 4H), 6.80(dd, 1H), 6.93(dd, 1H), 7.13(dd, 1H) |
| 7.14 | Propyl | Tetrahydropyran-3-yl | Thien-2-yl | 3.80–4.15(m, 4H), 6.80(dd, 1H), 6.93(dd, 1H), 7.13(dd, 1H) |
| 7.15 | Ethyl | Tetrahydropyran-4-yl | Thien-2-yl | 3.90–4.23(m, 4H), 6.80(dd, 1H), 6.93(dd, 1H), 7.13(dd, 1H) |
| 7.16 | Propyl | Tetrahydropyran-4-yl | Thien-2-yl | 3.90–4.23(m, 4H), 6.80(dd, 1H), 6.93(dd, 1H), 7.13(dd, 1H) |
| 7.17 | Ethyl | Tetrahydrothiopyran-3-yl | Thien-2-yl | 4.06(m, 2H), 6.80(dd, 1H), 6.93(dd, 1H), 7.13(dd, 1H) |
| 7.18 | Propyl | Tetrahydrothiopyran-3-yl | Thien-2-yl | 4.06(m, 2H), 6.80(dd, 1H), 6.93(dd, 1H), 7.13(dd, 1H) |
| 7.19 | Ethyl | Tetrahydropyran-3-yl | 5-Methylthien-2-yl | 3.85–4.13(m, 4H), 6.53(s, 2H) |
| 7.20 | Propyl | Tetrahydropyran-3-yl | 5-Methylthien-2-yl | 3.80–4.13(m, 4H), 6.53(s, 2H) |
| 7.21 | Ethyl | Tetrahydropyran-4-yl | 5-Methylthien-2-yl | 3.90–4.15(m, 4H), 6.50(s, 2H) |
| 7.22 | Propyl | Tetrahydropyran-4-yl | 5-Methylthien-2-yl | 3.94–4.15(m, 4H), 6.53(s, 2H) |
| 7.23 | Ethyl | Tetrahydrothiopyran-3-yl | 5-Methylthien-2-yl | 4.08(m, 2H), 6.55(s, 2H) |
| 7.24 | Propyl | Tetrahydrothiopyran-3-yl | 5-Methylthien-2-yl | 4.08(m, 2H), 6.56(s, 2H) |

TABLE 7-continued

Structure: R² substituted cyclohexenone with OH, C(R¹)=N-O-(CH₂)₄-W, and ketone

I (W = Z—X$_n$)

| No. | R¹ | R² | W | Phys. data NMR data in ppm mp in °C. |
|---|---|---|---|---|
| 7.25 | Ethyl | Tetrahydropyran-3-yl | 5-Chlorothien-2-yl | 3.93(m, 2H), 4.10(m, 2H), 6.53 (d, 1H), 6.70(d, 1H) |
| 7.26 | Propyl | Tetrahydropyran-3-yl | 5-Chlorothien-2-yl | 3.93(m, 2H), 4.10(m, 2H), 6.53 (d, 1H), 6.70(d, 1H) |
| 7.27 | Ethyl | Tetrahydropyran-4-yl | 5-Chlorothien-2-yl | 3.90–4.10(m, 4H), 6.53(m, 1H), 6.70(d, 1H) |
| 7.28 | Propyl | Tetrahydropyran-4-yl | 5-Chlorothien-2-yl | 3.90–4.10(m, 4H), 6.53(d, 1H), 6.70(d, 1H) |
| 7.29 | Ethyl | Tetrahydrothiopyran-3-yl | 5-Chlorothien-2-yl | 4.10(m, 2H), 6.53(d, 1H), 6.70(d, 1H) |
| 7.30 | Propyl | Tetrahydrothiopyran-3-yl | 5-Chlorothien-2-yl | 4.10(m, 2H), 6.53(d, 1H), 6.70(d, 1H) |
| 7.31 | Ethyl | Tetrahydropyran-3-yl | 5-Ethylthien-2-yl | 3.80–4.09(m, 4H), 6.60(s, 2H) |
| 7.32 | Propyl | Tetrahydropyran-3-yl | 5-Ethylthien-2-yl | 3.80–4.09(m, 4H), 6.60(s, 2H) |
| 7.33 | Ethyl | Tetrahydropyran-4-yl | 5-Ethylthien-2-yl | 3.93–4.09(m, 4H), 6.60(s, 2H) |
| 7.34 | Propyl | Tetrahydropyran-4-yl | 5-Ethylthien-2-yl | 3.93–4.09(m, 4H), 6.60(s, 2H) |
| 7.35 | Ethyl | Tetrahydrothiopyran-3-yl | 5-Ethylthien-2-yl | 4.03(m, 2H), 6.60(s, 2H) |
| 7.36 | Propyl | Tetrahydrothiopyran-3-yl | 5-Ethylthien-2-yl | 4.03(m, 2H), 6.60(s, 2H) |
| 7.37 | Ethyl | Tetrahydropyran-3-yl | 1-Methylpyrrol-2-yl | 64–66 |
| 7.38 | Propyl | Tetrahydropyran-3-yl | 1-Methylpyrrol-2-yl | 3.90(m, 2H), 4.09(t, 2H), 5.87 (m, 1H), 6.03(m, 1H), 6.53(m, 1H) |
| 7.39 | Ethyl | Tetrahydropyran-4-yl | 1-Methylpyrrol-2-yl | 82–84 |
| 7.40 | Propyl | Tetrahydropyran-4-yl | 1-Methylpyrrol-2-yl | 4.00(m, 22), 4.09(t, 2H), 5.87 (m, 1H), 6.03(m, 1H), 6.53(m, 1H) |
| 7.41 | Ethyl | Tetrahydrothiopyran-3-yl | 1-Methylpyrrol-2-yl | 4.09(t, 2H), 5.87(m, 1H), 6.03 (m, 1H), 6.53(m, 1H) |
| 7.42 | Propyl | Tetrahydrothiopyran-3-yl | 1-Methylpyrrol-2-yl | 4.09(t, 2H), 5.87(m, 1H), 6.03 (m, 1H), 6.53(m, 1H) |

TABLE 8

Structure: R² substituted cyclohexenone with OH, C(R¹)=N-O-CH₂CH₂CH=CH-W, and ketone I (W = Z—X$_n$)

| No. | R¹ | R² | W | Phys. data NMR data in ppm mp in °C. |
|---|---|---|---|---|
| 8.01 | Ethyl | Tetrahydropyran-4-yl | Furan-2-yl | 4.13(t, 2H), 6.00–6.42(m, 4H), 7.33(bs, 1H) |
| 8.02 | Ethyl | Tetrahydropyran-3-yl | Furan-3-yl | 4.13(t, 2H), 5.92(m, 1H), 6.33(d, 1H), 6.55(bs, 1H) 7.40(d, 2H) |
| 8.03 | Ethyl | Tetrahydropyran-4-yl | Furan-3-yl | 4.13(m, 2H), 5.92(m, 1H), 6.33(d, 1H), 6.55(s, 1H) 7.40(d, 2H) |
| 8.04 | Ethyl | Tetrahydrothiopyran-3-yl | Furan-3-yl | 4.13(m, 2H), 5.92(m, 1H), 6.33(d, 1H), 6.55(s, 1H) 7.40(d, 2H) |
| 8.05 | Ethyl | Tetrahydropyran-3-yl | Thien-2-yl | 4.15(t, 2H), 6.00(dt, 1H), 6.60(d, 1H), 6.90(m, 2H) 7.10(d, 1H) |
| 8.06 | Propyl | Tetrahydropyran-3-yl | Thien-2-yl | 4.10(t, 2H), 6.00(dt, 1H), 6.60(d, 1H), 6.80–7.20(m, 3H) |
| 8.07 | Ethyl | Tetrahydropyran-4-yl | Thien-2-yl | 4.15(t, 2H), 6.00(dt, 1H), 6.60(d, 1H), 6.80–7.20(m, 3H) |
| 8.08 | Propyl | Tetrahydropyran-4-yl | Thien-2-yl | 4.15(t, 2H), 6.00(dt, 1H), 6.60(d, 1H), 6.80–7.20(m, 3H) |
| 8.09 | Ethyl | Tetrahydrothiopyran-3-yl | Thien-2-yl | 4.15(t, 2H), 6.00(dt, 1H), 6.60(d, 1H), 6.80–7.20(m, 3H) |
| 8.10 | Propyl | Tetrahydrothiopyran-3-yl | Thien-2-yl | 4.15(t, 2H), 6.00(dt, 1H), 6.60(d, 1H), 6.80–7.20(m, 3H) |
| 8.11 | Ethyl | 2,4,6-Trimethylphenyl | Thien-2-yl | 4.20(t, 2H), 6.10(dt, 1H), |

TABLE 8-continued

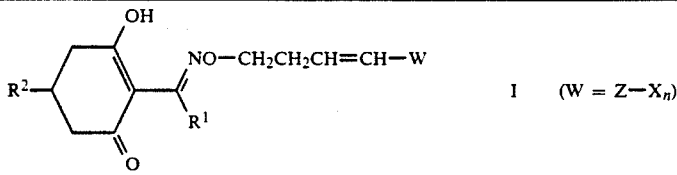

I (W = Z—X$_n$)

| No. | R$^1$ | R$^2$ | W | Phys. data NMR data in ppm mp in °C. |
|---|---|---|---|---|
| | | | | 6.60(d, 1H), 6.80–7.20(m, 5H) |
| 8.12 | Ethyl | Tetrahydropyran-3-yl | 5-Methylthien-2-yl | 4.13(t, 2H), 5.87(dt, 1H) 6.37–6.73(m, 3H) |
| 8.13 | Propyl | Tetrahydropyran-3-yl | 5-Methylthien-2-yl | 4.13(t, 2H), 5.87(dt, 1H) 6.37–6.73(m, 3H) |
| 8.14 | Ethyl | Tetrahydropyran-4-yl | 5-Methylthien-2-yl | 4.13(t, 2H), 5.87(dt, 1H) 6.37–6.73(m, 3H) |
| 8.15 | Propyl | Tetrahydropyran-4-yl | 5-Methylthien-2-yl | 4.13(t, 2H), 5.87(dt, 1H) 6.37–6.73(m, 3H) |
| 8.16 | Ethyl | Tetrahydrothiopyran-3-yl | 5-Methylthien-2-yl | 4.13(t, 2H), 5.88(dt, 1H) 6.37–6.73(m, 3H) |
| 8.17 | Propyl | Tetrahydrothiopyran-3-yl | 5-Methylthien-2-yl | 4.13(t, 2H), 5.88(dt, 1H) 6.37–6.73(m, 3H) |
| 8.18 | Ethyl | Tetrahydropyran-3-yl | 5-Chlorothien-2-yl | 4.15(t, 2H), 5.93(dt, 1H), 6.46(d, 1H), 6.63(d, 1H), 6.75(d, 1H) |
| 8.19 | Propyl | Tetrahydropyran-3-yl | 5-Chlorothien-2-yl | 4.15(t, 2H), 5.93(dt, 1H), 6.46(d, 1H), 6.63(d, 1H), 6.75(d, 1H) |
| 8.20 | Ethyl | Tetrahydropyran-4-yl | 5-Chlorothien-2-yl | 4.15(t, 2H), 5.93(dt, 1H), 6.46(d, 1H), 6.63(d, 1H), 6.75(d, 1H) |
| 8.21 | Propyl | Tetrahydropyran-4-yl | 5-Chlorothien-2-yl | 4.15(t, 2H), 5.93(dt, 1H), 6.46(d, 1H), 6.63(d, 1H), 6.75(d, 1H) |
| 8.22 | Ethyl | Tetrathiohydropyran-3-yl | 5-Chlorothien-2-yl | 4.15(t, 2H), 5.93(dt, 1H), 6.46(d, 1H), 6.63(d, 1H), 6.75(d, 1H) |
| 8.23 | Propyl | Tetrathiohydropyran-3-yl | 5-Chlorothien-2-yl | 4.15(t, 2H), 5.93(dt, 1H), 6.46(d, 1H), 6.63(d, 1H), 6.75(d, 1H) |
| 8.24 | Ethyl | Tetrahydropyran-3-yl | Thien-3-yl | 4.15(t, 2H), 6.07(dt, 1H), 6.50(d, 1H), 7.00–7.32(m, 3H) |
| 8.25 | Propyl | Tetrahydropyran-3-yl | Thien-3-yl | 4.15(t, 2H), 6.07(dt, 1H), 6.50(d, 1H), 7.00–7.32(m, 3H) |
| 8.26 | Ethyl | Tetrahydropyran-4-yl | Thien-3-yl | 4.20(t, 2H), 6.07(dt, 1H), 6.50(d, 1H), 7.03–7.32(m, 3H) |
| 8.27 | Propyl | Tetrahydropyran-4-yl | Thien-3-yl | 4.20(t, 2H), 6.07(dt, 1H), 6.50(d, 1H), 7.03–7.32(m, 3H) |
| 8.28 | Ethyl | Tetrahydrothiopyran-3-yl | Thien-3-yl | 4.17(t, 2H), 6.07(dt, 1H), 6.50(d, 1H), 7.00–7.36(m, 3H) |
| 8.29 | Propyl | Tetrahydrothiopyran-3-yl | Thien-3-yl | 4.17(t, 2H), 6.07(dt, 1H), 6.50(d, 1H), 7.00–7.36(m, 3H) |
| 8.30 | Ethyl | Tetrahydropyran-3-yl | 2-Chlorothien-3-yl | 4.20(t, 2H), 6.10(dt, 1H), 6.52(d, 1H), 7.05(s, 2H), |
| 8.31 | Propyl | Tetrahydropyran-3-yl | 2-Chlorothien-3-yl | 4.20(t, 2H), 6.10(dt, 1H), 6.52(d, 1H), 7.05(s, 2H), |
| 8.32 | Ethyl | Tetrahydropyran-4-yl | 2-Chlorothien-3-yl | 4.20(t, 2H), 6.13(dt, 1H), 6.52(d, 1H), 7.07(s, 2H), |
| 8.33 | Propyl | Tetrahydropyran-4-yl | 2-Chlorothien-3-yl | 4.20(t, 2H), 6.13(dt, 1H), 6.52(d, 1H), 7.07(s, 2H), |
| 8.34 | Ethyl | Tetrahydrothiopyran-3-yl | 2-Chlorothien-3-yl | 4.20(t, 2H), 6.12(dt, 1H), 6.53(d, 1H), 7.10(s, 2H), |
| 8.35 | Propyl | Tetrahydrothiopyran-3-yl | 2-Chlorothien-3-yl | 4.20(t, 2H), 6.12(dt, 1H), 6.53(d, 1H), 7.10(s, 2H), |
| 8.36 | Ethyl | Tetrahydropyran-3-yl | 5-Chlorothien-3-yl | 4.17(t, 2H), 6.00(dt, 1H), 6.33(d, 1H), 6.83(s, 1H), 7.03(s, 1H) |
| 8.37 | Propyl | Tetrahydropyran-3-yl | 5-Chlorothien-3-yl | 4.17(t, 2H), 6.00(dt, 1H), 6.33(d, 1H), 6.83(s, 1H), 7.03(s, 1H) |
| 8.38 | Ethyl | Tetrahydropyran-4-yl | 5-Chlorothien-3-yl | 4.17(t, 2H), 6.00(dt, 1H), 6.33(d, 1H), 6.83(s, 1H), 7.03(s, 1H) |
| 8.39 | Propyl | Tetrahydropyran-4-yl | 5-Chlorothien-3-yl | 4.17(t, 2H), 6.00(dt, 1H), 6.33(d, 1H), 6.83(s, 1H), 7.03(s, 1H) |
| 8.40 | Ethyl | Tetrahydrothiopyran-3-yl | 5-Chlorothien-3-yl | 4.20(t, 2H), 6.00(dt, 1H), 6.33(d, 1H), 6.83(s, 1H), 7.03(s, 1H) |

TABLE 8-continued

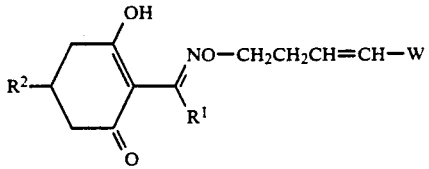

I   (W = Z—$X_n$)

| No. | $R^1$ | $R^2$ | W | Phys. data NMR data in ppm mp in °C |
|---|---|---|---|---|
| 8.41 | Propyl | Tetrahydrothiopyran-3-yl | 5-Chlorothien-3-yl | 4.20(t, 2H), 6.00(dt, 1H), 6.33(d, 1H), 6.83(s, 1H), 7.03(s, 1H) |

TABLE 9

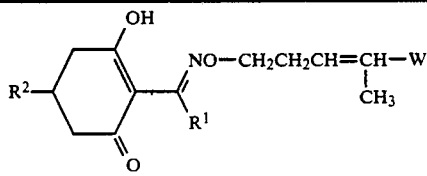

I   (W = Z—$X_n$)

| No. | $R^1$ | $R^2$ | W | Phys. Data NMR Data in ppm mp in °C |
|---|---|---|---|---|
| 9.01 | Ethyl | Tetrahydropyran-3-yl | Thien-2-yl | 3.90(m, 2H), 6.90(m, 2H), 7.10(d, 1H) |
| 9.02 | Propyl | Tetrahydropyran-3-yl | Thien-2-yl | 3.90(m, 2H), 6.90(m, 2H), 7.10(d, 1H) |
| 9.03 | Ethyl | Tetrahydropyran-4-yl | Thien-2-yl | |
| 9.04 | Propyl | Tetrahydropyran-4-yl | Thien-2-yl | |
| 9.05 | Ethyl | Tetrahydrothiopyran-3-yl | Thien-3-yl | 6.90(m, 2H), 7.10(d, 1H) |
| 9.06 | Propyl | Tetrahydrothiopyran-3-yl | Thien-3-yl | 6.90(m, 2H), 7.10(d, 1H) |

TABLE 10

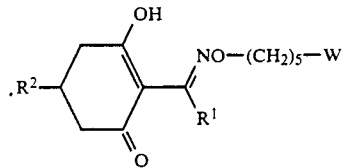

I   (W = Z—$X_n$)

| No. | $R^1$ | $R^2$ | W | Phys. Data NMR Data in ppm mp in °C |
|---|---|---|---|---|
| 10.01 | Ethyl | Tetrahydropyran-3-yl | Furan-2-yl | 5.93(m, 1H), 6.27(m, 1H), 7.27(m, 1H) |
| 10.02 | Propyl | Tetrahydropyran-3-yl | Furan-2-yl | 5.93(m, 1H), 6.27(m, 1H), 7.27(m, 1H) |
| 10.03 | Ethyl | Tetrahydropyran-4-yl | Furan-2-yl | 5.90(m, 1H), 6.24(m, 1H), 7.24(m, 1H) |
| 10.04 | Propyl | Tetrahydropyran-4-yl | Furan-2-yl | 50–53 |
| 10.05 | Ethyl | Tetrahydrothiopyran-3-yl | Furan-2-yl | 5.93(m, 1H), 6.27(m, 1H), 7.27(m, 1H) |
| 10.06 | Propyl | Tetrahydrothiopyran-3-yl | Furan-2-yl | 5.93(m, 1H), 6.27(m, 1H), 7.27(m, 1H) |
| 10.07 | Ethyl | Tetrahydropyran-3-yl | Thien-2-yl | 43–45 |
| 10.08 | Propyl | Tetrahydropyran-3-yl | Thien-2-yl | 73–75 |
| 10.09 | Ethyl | Tetrahydropyran-4-yl | Thien-2-yl | 91–93 |
| 10.10 | Propyl | Tetrahydropyran-4-yl | Thien-2-yl | 74–75 |
| 10.11 | Ethyl | Tetrahydrothiopyran-3-yl | Thien-2-yl | 4.07(t, 2H), 6.80(m, 1H), 6.90 (m, 1H), 7.10(m, 1H) |
| 10.12 | Propyl | Tetrahydrothiopyran-3-yl | Thien-2-yl | 4.07(t, 2H), 6.80(m, 1H), 6.90 (m, 1H), 7.10(m, 1H) |
| 10.13 | Ethyl | Tetrahydropyran-3-yl | 1-Methylpyrrol-2-yl | 3.90(m, 2H), 4.12(t, 2H), 5.90 (m, 1H), 6.06(m, 1H), 6.53(m, 1H) |
| 10.14 | Propyl | Tetrahydropyran-3-yl | 1-Methylpyrrol-2-yl | 3.90(m, 2H), 4.12(t, 2H), 5.90 (m, 1H), 6.06(m, 1H), 6.53(m, 1H) |
| 10.15 | Ethyl | Tetrahydropyran-4-yl | 1-Methylpyrrol-2-yl | 4.00(m, 2H), 4.12(t, 2H), 5.90 (m, 1H), 6.06(m, 1H), 6.53(m, 1H) |
| 10.16 | Propyl | Tetrahydropyran-4-yl | 1-Methylpyrrol-2-yl | 4.00(m, 2H), 4.12(t, 2H), 5.90 |

TABLE 10-continued

Structure: cyclohexenone with OH, R² substituent, C(R¹)=N-O-(CH₂)₅-W, and ketone; I (W = Z-X$_n$)

| No. | R¹ | R² | W | Phys. Data NMR Data in ppm mp in °C. |
|---|---|---|---|---|
| 10.17 | Ethyl | Tetrahydrothiopyran-3-yl | 1-Methylpyrrol-2-yl | (m, 1H), 6.06(m, 1H), 6.53(m, 1H) 4.12(t, 2H), 5.90(m, 1H), 6.06(m, 1H), 6.53(m, 1H) |
| 10.18 | Propyl | Tetrahydrothiopyran-3-yl | 1-Methylpyrrol-2-yl | 4.12(t, 2H), 5.90(m, 1H), 6.06(m, 1H), 6.53(m, 1H) |

TABLE 11

Structure: cyclohexenone with OH, R² substituent, C(R¹)=N-O-(CH₂)₆-W, and ketone; I (W = Z-X$_n$)

| No. | R¹ | R² | W | Phys. Data NMR Data in ppm mp in °C. |
|---|---|---|---|---|
| 11.01 | Ethyl | Tetrahydropyran-3-yl | Furan-2-yl | 5.90(m, 1H), 6.27(m, 1H), 7.27(m, 1H) |
| 11.02 | Propyl | Tetrahydropyran-3-yl | Furan-2-yl | 5.90(m, 1H), 6.27(m, 1H), 7.27(m, 1H) |
| 11.03 | Ethyl | Tetrahydropyran-4-yl | Furan-2-yl | 5.93(m, 1H), 6.27(m, 1H), 7.27(m, 1H) |
| 11.04 | Propyl | Tetrahydropyran-4-yl | Furan-2-yl | 5.93(m, 1H), 6.27(m, 1H), 7.27(m, 1H) |
| 11.05 | Ethyl | Tetrahydrothiopyran-3-yl | Furan-2-yl | 5.93(m, 1H), 6.27(m, 1H), 7.27(m, 1H) |
| 11.06 | Propyl | Tetrahydrothiopyran-3-yl | Furan-2-yl | 5.93(m, 1H), 6.27(m, 1H), 7.27(m, 1H) |
| 11.07 | Ethyl | Tetrahydropyran-3-yl | Thien-2-yl | 6.77(m, 1H), 6.90(m, 1H), 7.10(m, 1H) |
| 11.08 | Propyl | Tetrahydropyran-3-yl | Thien-2-yl | 6.77(m, 1H), 6.90(m, 1H), 7.10(m, 1H) |
| 11.09 | Ethyl | Tetrahydropyran-4-yl | Thien-2-yl | 50-52 |
| 11.10 | Propyl | Tetrahydropyran-4-yl | Thien-2-yl | 6.80(m, 1H), 6.90(m, 1H), 7.10(m, 1H) |
| 11.11 | Ethyl | Tetrahydrothiopyran-3-yl | Thien-2-yl | 6.80(m, 1H), 6.90(m, 1H), 7.10(m, 1H) |
| 11.12 | Propyl | Tetrahydrothiopyran-3-yl | Thien-2-yl | 6.80(m, 1H), 6.90(m, 1H), 7.10(m, 1H) |
| 11.13 | Ethyl | Tetrahydropyran-3-yl | 1-Methylpyrrol-2-yl | 5.90(m, 1H), 6.06(m, 1H), 6.53(m, 1H) |
| 11.14 | Propyl | Tetrahydropyran-3-yl | 1-Methylpyrrol-2-yl | 5.90(m, 1H), 6.06(m, 1H), 6.53(m, 1H) |
| 11.15 | Ethyl | Tetrahydropyran-4-yl | 1-Methylpyrrol-2-yl | 5.87(m, 1H), 6.06(m, 1H) 6.53(m, 1H) |
| 11.16 | Propyl | Tetrahydropyran-4-yl | 1-Methylpyrrol-2-yl | 5.87(m, 1H), 6.06(m, 1H), 6.53(m, 1H) |
| 11.17 | Ethyl | Tetrahydrothiopyran-3-yl | 1-Methylpyrrol-2-yl | 5.90(m, 1H), 6.06(m, 1H), 6.50(m, 1H) |
| 11.18 | Propyl | Tetrahydrothiopyran-3-yl | 1-Methylpyrrol-2-yl | 5.90(m, 1H), 6.06(m, 1H), 6.50(m, 1H) |

USE EXAMPLES

The action of the cyclohexenone derivatives of the formula I on plant growth is demonstrated in greenhouse experiments:

The vessels employed were plastic flowerpots having a volume of 300 cm³ and filled with a sandy loam containing about 3.0% humus. The seeds of the test plants were sown separately, according to species.

For the preemergence treatment, the formulated active ingredients were applied to the surface of the soil immediately after the seeds had been sown. The compounds were emulsified or suspended in water as vehicle, and sprayed through finely distributing nozzles.

After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the plants were grown, depending on growth form, to a height of 3 to 15 cm before being treated with the compounds, suspended or emulsified in water. The application rate for post-emergence treatment was 0.25 kg/ha.

The pots were set up in the greenhouse, heat-loving species at 20° to 35° C., and species from moderate climates at 10 to 25° C.. The experiments were run for from 2 to 4 weeks. During this period the plants were tended and their reactions to the various treatments assessed. The assessment scale was 0 to 100, 100 denoting nonemergence or complete destruction of at least the visible plant parts, and 0 denoting no damage or normal growth.

The plants used in the experiments were *Oryza sativa* and *Setaria*. Compound 8.08, applied postemergence at a rate of 0.25 Kg/ha, combated unwanted grassy plants very well, and was at the same time tolerated by rice as an example of a crop plant.

We claim:

1. A cyclohexenone oxime ether of the formula I

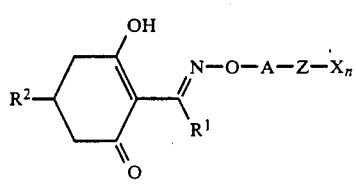

(I)

where $R^1$ is $C_1-C_6$-alkyl;

A is $C_2-C_6$-alkylene or $C_3-C_6$-alkenylene, where these groups may carry from one to three $C_1-C_3$-alkyl groups or halogen atoms;

Z is a 5-membered heteroaromatic structure having from one to three hetero atoms selected from the group consisting of three nitrogen atoms and one oxygen or sulfur atom a 6-membered heteroaromatic structure having from one to four nitrogen atoms;

X is an amino group $—NR^a R^b$, where $R^1$ is hydrogen, $C_1-C_4$-alkyl, $C_3-C_6$-alkenyl or $C_3-C_6$-alkynyl $R^b$ is hydrogen, $C_1-C_4$-alkyl, $C_3-C_6$-alkenyl, $C_3-C_6$-alkynyl, $C_1-C_6$-acyl or benzoyl, where the aromatic ring may additionally carry from one to three of the following substituents: nitro, cyano, halogen, $C_1-C_4$-alkyl, $C_1-C_4$-alkoxy, $C_1-C_4$-alkylthio and $C_1-C_4$-haloalkyl, or X is nitro, cyano, halogen, $C_1-C_4$-alkyl, $C_1-C_4$-alkoxy, alkylthio, $C_1-C_4$-haloalkyl, $C_1-C_4$-haloalkoxy, carboxyl, $C_1-C_4$-alkoxycarbonyl, benzyloxycarbonyl or phenyl, where the aromatic radicals may additionally carry from one to three of the following substituents: nitro, cyano, halogen, $C_1-C_4$-alkyl, $C_1-C_4$-alkoxy, $C_1-C_4$-alkylthio, $C_1-C_4$-haloalkyl, $C_1-C_4$-haloalkoxy, carbonyl, $C_1-C_4$-alkoxycarbonyl or benzyloxycarbonyl, n is from 0 to 3, or from 1 to 4 where Z is halogen-substituted pyridyl, and $R^2$ is $C_1-C_4$-alkylthio-$C_1-C_6$-alkyl; $C_1-C_4$-alkylthio-$C_3-C_7$-cycloalkyl phenyl substituted by three $C_1-C_4$-alkyl groups, or its agriculturally useful salts and esters of $C_1-C_{10}$-carboxylic acids and inorganic acids.

2. A herbicidal composition containing a herbicidal amount of one or more compounds of the formula I as described in claim 1 and inert additives.

3. A method for controlling undesirable plant growth, wherein the undesirable plants and/or their habitat is or are treated with a herbicidal amount of a cyclohexenone derivative of the formula I as described in claim 1.

* * * * *

UNITED STATES PATENT AND TRADEMARK OFFICE
CERTIFICATE OF CORRECTION

PATENT NO.: 5,330,965

DATED: July 19, 1994

INVENTOR(S): MISSLITZ et al.

It is certified that error appears in the above-identified patent and that said Letters Patent is hereby corrected as shown below:

Claim 1, column 64, line 6, "$R^1$" should be --$R^a$--.

Claim 1, column 64, line 14, before "alkylthio" insert -- $C_1$-$C_4$- --.

Claim 1, column 64, line 21, "carbonyl" should be --carboxyl--.

Signed and Sealed this

Twenty-fifth Day of October, 1994

Attest:

BRUCE LEHMAN

Attesting Officer

Commissioner of Patents and Trademarks